(12) United States Patent
Bose

(10) Patent No.: US 10,385,083 B2
(45) Date of Patent: Aug. 20, 2019

(54) PHOSPHAPLATIN COMPLEXES AND METHODS FOR TREATMENT OF PROLIFERATIVE DISEASES USING THE PHOSPHAPLATIN COMPLEXES

(71) Applicant: Ohio University, Athens, OH (US)

(72) Inventor: Rathindra N. Bose, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 15/604,209

(22) Filed: May 24, 2017

(65) Prior Publication Data

US 2017/0327521 A1 Nov. 16, 2017

Related U.S. Application Data

(62) Division of application No. 13/701,313, filed as application No. PCT/US2011/038948 on Jun. 2, 2011, now Pat. No. 9,688,709.

(60) Provisional application No. 61/351,514, filed on Jun. 4, 2010.

(51) Int. Cl.
| C07F 15/00 | (2006.01) |
| A61K 31/555 | (2006.01) |
| A61K 33/24 | (2019.01) |

(52) U.S. Cl.
CPC ........ C07F 15/0093 (2013.01); A61K 31/555 (2013.01); A61K 33/24 (2013.01)

(58) Field of Classification Search
CPC .............. C07F 15/0086; C07F 15/0093; A61K 31/6615
See application file for complete search history.

(56) References Cited

U.S. PATENT DOCUMENTS

| 4,234,500 | A | 11/1980 | Hoeschele et al. |
| 4,291,027 | A | 9/1981 | Hoeschel et al. |
| 7,141,691 | B2 | 11/2006 | Kratz et al. |
| 7,342,122 | B2 | 3/2008 | Odani |
| 7,410,960 | B2 | 8/2008 | Fenton et al. |
| 7,700,649 | B2 * | 4/2010 | Bose ............... A61K 33/24 514/492 |
| 8,034,964 | B2 | 10/2011 | Bose |
| 8,445,710 | B2 | 5/2013 | Bose |
| 8,653,132 | B2 | 2/2014 | Bose |
| 9,012,669 | B2 | 4/2015 | Bose et al. |
| 9,688,709 | B2 | 6/2017 | Bose |
| 2007/0160656 | A1 | 7/2007 | Dziewiszek et al. |
| 2009/0042838 | A1 * | 2/2009 | Bose ............... A61K 33/24 514/106 |

FOREIGN PATENT DOCUMENTS

| EP | 0409527 | 1/1991 |
| EP | 2177525 | 4/2010 |
| GB | 2043642 | 10/1980 |
| JP | 55120594 | 9/1980 |
| JP | 2005501803 | 1/2005 |
| JP | 2006520360 | 9/2006 |
| JP | 2006525368 | 11/2006 |
| JP | 2007521257 | 8/2017 |
| WO | 2005000858 | 1/2005 |
| WO | 2009021081 | 2/2009 |
| WO | 2009021082 | 2/2009 |
| WO | 2011125911 | 10/2011 |
| WO | 2011153365 | 12/2011 |
| WO | 2012096722 | 7/2012 |

OTHER PUBLICATIONS

Notice of Allowance in JP 2010-520294, dated Sep. 10, 2013 (with translation).
Office Action in JP 2010-520294, dated Jul. 23, 2013 (with translation).
Office Action in JP 2010-520294, dated Mar. 26, 2013 (with translation).
Office Action in JP 2010-520294, dated Oct. 30, 2012 (with translation).
Folkman et al., "Angiogenesis in cancer, vascular, rheumatoid and other disease," Nat. Med., 1:27-31 (1995).
Rosenberg et al., "Platinum Compounds: a New Class of Potent Antitumour Agents," Nature, vol. 222, 385-386 (1969).
Office Action in corresponding application NZ603952, dated Aug. 2, 2013 (1 page). International Search Report and Written Opinion in PCT/US2008/072398, dated Mar. 5, 2009 (10 pages).
Extended European Search Report in EP08797320.2, dated Sep. 28, 2010 (7 pages).
Extended European Search Report in EP13182512, dated Oct. 23, 2013 (9 pages).
International Search Report and Written Opinion in PCT/US2011/038948, dated Nov. 18, 2011.
International Search Report and Written Opinion in PCT/US2011/063139, dated Mar. 8, 2012.
Abe et al., "PTEN Decreases in Vivo Vascularization of Experimental Gliomas in Spite of Proangiogenic Stimuli," Cancer Research, 63, 2300-2305 (2003).
Appleton TG et al., "Multinuclear NMR study of reactions of methylphosphonic acid, CH3PO3H2, and (aminoalkyl) phosphonic acids, NH2(CH2)nPO3H2 (n=1-3), with the cis-diamminediaquaplatinum(II) cation and cis-diamminedihydroxoplatinum(II)," Inorganic Chemistry, 25:720-725 (1986).

(Continued)

*Primary Examiner* — Pancham Bakshi
(74) *Attorney, Agent, or Firm* — Dinsmore & Shohl, LLP

(57) ABSTRACT

Stable monomeric phosphaplatins, namely, (pyrophosphato) platinum(II) or platinum(IV) complexes containing a cis-cyclohexanediamine ligand or enantiomerically enriched or enantiopure trans-cyclohexanediamine ligands, and synthesis of these complexes, are provided. Efficacies and toxicities of the phosphaplatin compounds are determined toward a variety of cancers, including sensitive and resistant ovarian cancers, head and neck, and colon cancers. Compositions comprising the platinum complexes, and methods for treatment of proliferative diseases or disorders by means of the complexes or the compositions comprising them are disclosed.

16 Claims, 7 Drawing Sheets

(56) References Cited

OTHER PUBLICATIONS

Belka C et al., "Why 'radiation oncology,'" Radiat Oncol, 1:1 (2006).

Beneteau, Marie et al., "Localization of Fas/CD95 into the Lipid Rafts on Down-Modulation of the Phosphatidylinositol 3-Kinase Signaling Pathway," Mol Cancer Res 2008; 6(4), 604-613 (Apr. 2008).

Birchmeier et al., "Cadherin expression in carcinomas: role in the formation of cell junctions and the prevention of invasiveness," Biochim. Biophys. Acta, 1198, 11-26 (1994).

Bose, Abstract, "Development of Effective Cancer Therapeutics With Reduced Toxicity by Targeting Anti-Apoptotic Cell Surface Receptor Genes," BIT Life Sciences 3rd Annual World Congress of Genes (2009).

Bose et al., Poster, "Platinum-(IV) Phosphato Complexes as Potential Anticancer Drugs," displayed at ACS National Meeting, Sep. 10-14, 2006.

Bose et al., Poster, "Platinum Phosphato Complexes: How They Might Work as Anticancer Agents," displayed ACS National Meeting, Mar. 25, 2007.

Bose et al., "Kinetics and Mechanisms of Platinum (II) Promoted Hydrolysis of Inorganic Polyphosphates," CAPLUS 1985, XP002315775.

Bose et al., "Kinetics and Mechanisms of Platinum (II) Promoted Hydrolysis of Inorganic Polyphosphates," Inorg. Chem., 24, 3989-3996 (1985).

Bose et al., "Multinuclear NMR Studies and the Kinetics of Formation of Platinum (II)-Adenine Nucleotide Complexes," J. Am. Chem. Society, 1986, 108, 4403-4408.

Bose et al., "Non-DNA Binding Platinum Anticancer Agents: Cytotoxic Activities of Platinum-phosphato Complexes Towards Human Ovarian Cancer Cells," PNAS, vol. 105, No. 47, 18314-18319, Nov. 19, 2008 (web).

Bose et al., "Phosphorus-31 NMR and Kinetic Studies of the Formation of Ortho-, Pyro- and Tri-phosphato Complexes of cis-Dichlorodiammineplatinum (II)," J. Am. Chem. Soc., 106, 3336-3343 (1984).

Bose et al., "Phosphato Complexes of Platinum (II): Phosphorus-31 NMR and Kinetics of Formation and Isomerization Studies," Inorg. Chem., 29, 3461-3467 (1990).

Bose et al., "Platinum (II) Catalyzed Hydrolysis of Pyrophosphate and Triphosphate: Phosphorus-31 NMR characterization of Kinetic Intermediates," Inorg. Chem., 23, 1181-1183 (1984).

Calvert et al., "Early Clinical Studies with cis-Diammine-1,1-Cyclobutane Dicarboxylate Platinum II," Cancer Chemother Pharmacol 9: 140-147 (1982).

Carmeliet, P., "Angiogenesis in life, disease, and medicine," Nature 438, 932-936 (2005).

Cavallaro et al., "Cadherins and the tumour progression: is it all in a switch?," Cancer Letters, 176, 123-128 (2002).

Christian et al., Abstract #291, "Phase I and Pharmacologic Study of Ormaplatin (OP)/Tetraplatin," Proceedings of ASCO, vol. 11, Mar. 1992.

Coll M et al., "Molecular structure of the complex formed between the anticancer drug cisplatin and d(pGpG):C222(1) crystal form," J Biomol Struct Dyn, 8:315-330 (1990).

Moghaddas et al., Abstract, "Superior Efficacy of Phosphoplatins: Novel Non-DNA-Binding Platinum Drugs for Human Ovarian Cancer," (2010).

Creaven, et al., "Phase I Clinical Trial of cis-Dichloro-trans-dihydroxy-bis-isopropylamine platinum (IV) (CHIP)," Cancer Treat Rep 67: 795-800 (1983).

Dezvareh et al., Poster, "In vitro and In vivo Efficacy and Toxicity Studies of Non-DNA Binding Class of Platinum Anticancer Complexes in the Treatment of Resistant Ovarian Cancer Cell Line," displayed at Ohio University Student Expo (May 23, 2011).

Eastman, A., "Activation of Programmed Cell Death by Anticancer Agents: Cisplatin as a Model System," Cancer Cells, vol. 2, No. 8-9, 275-280 (1990).

Eiyassaki et al., "Lipid-rafts mediate ultraviolet light-induced fas aggregation in M624 melanoma cells," Photochemistry and Photobiology, 82:787-792 (2006).

Extra et al., "Phase I study of oxaliplatin in patients with advanced cancer," Cancer Chemother Pharmacol 25: 299-303 (1990).

Ohgaki et al., "Genetic pathways to primary and secondary glioblastoma," Am. J. Pathol, 170: 1445-1453 (2007).

Frixen et al., "E-Cadherin-mediated Cell-Cell Adhesion Prevents Invasiveness of Human Carcinoma Cells," J. Cell. Biol., 113, 173-185 (1991).

Gajate, Consuelo et al., "Lipid raft connection between extrinsic and intrinsic apoptotic pathways," Biochemical and Biophysical Research Communications 380, 780-784 (2009).

Galanski M., "Recent developments in the field of anticancer platinum complexes," Recent Pat Anticancer Drug Discov, 1:285-295 (2006).

Giaver et al., "Chemogenomic profiling: identifying the functional interactions of small molecules in yeast," Proc Natl Acad Sci USA, 101, 793-8 (2004).

Giaver et al., "Functional profiling of the Saccharomyces cerevisiae genome," Nature, 418, 387-91 (2002).

Gill et al., Synthesis, Kinetics, and Mechanism of Formation of Polynuclear Hydroxo-Bridged Complexes of (trans-1,2,-Diaminocyclohexane) platinum (II), J. Am. Chem. Soc., 104, 4598-4604 (1982).

Girnun GD et al., "Regression of drug-resistant lung cancer by the combination of rosiglitazone and carboplatin," Clin Cancer Res, 14:6478-6486 (2008).

Huang H et al., "Solution structure of a cisplatin-induced DNA interstrand cross-link," Science, 270:1842-1845 (1995).

Ishida S et al., "Uptake of the anticancer drug cisplatin mediated by the copper transporter Ctr1 in yeast and mammals," Proc Natl Acad Sci USA, 99:14298-14302 (2002).

Jamieson ER et al., "Structure, recognition, and processing fo cisplatin-DNA adducts," Chem Rev, 99:2467-2498 (1999).

Jemal A et al., "Cancer statitistics 2005," CA Cancer J Clin, 55:10-30 (2005).

Kelland et al., "Preclinical Antitumor Evaluation of Bis-acetato-ammine-dichloro-cyclohexylamine Platinum (IV): an Orally Active Platinum Drug," Cancer Research, 53, 2581-2586 (1993).

Komatsu M et al., "Copper-transporting P-type adenosine triphosphatase (ATP7B) is associated with cisplatin resistance," Cancer Res, 60:1312-1316 (2000).

Lee et al., "Genome-wide requirements for resistance to functionally distinct DNA-damaging agents," PLoS Genetics, 235-245 (2005).

Liu et al., "Targeting the phosphoinositide 3-kinase patway in cancer," Nature review (Drug Discovery), 8, 627-644 (2009).

Mishur et al., Abstract, "INOR 135 Platinum-(IV) phosphato complexes as potential anticancer drugs," displayed at ACS National Meeting, Sep. 10-14, 2006 (posted on ACS website Jul. 17, 2006).

Mishur, Robert J., Dissertation: "Synthesis, Characterization, Redox Kinetics, and Assessment of DNA and Thiol Binding of a new Class of Platinum(II) and -(IV) Pyrophosphato Complexes," 197 pages (Dec. 2008).

Mishur et al., "Synthesis, X-ray Chrystallographic, and NMR Characterizations of Platinum (II) and Platinum (IV) Pyrophosphato Complexes," Inorg. Chem., 47 (18), 7972-7982, Aug. 9, 2008 (web).

Office Action dated Jan. 20, 2015 pertaining to Japanese Patent Application No. 2013-513350.

Sherman et al., "Structural Aspects of Platinum Aticancer Drug Interactions with DNA," Chem. Rev., 87, 1153-1181 (1987).

Office Action from AP Appln. No. AP/P/2012/006594 dated Oct. 4, 2014.

Office Action dated Nov. 26, 2014 pertaining to Mexican Patent Application No. MX/a/2012/014174.

Office Action dated Dec. 1, 2014 pertaining to Chinese Patent Application No. 2011800387165.

Examination Report dated Mar. 5, 2015 pertaining to European Patent Application No. 11 726 567.8.

Patent Examination Report No. 1 dated Apr. 28, 2014 pertaining to Australian Patent Application No. 2011261381.

(56) References Cited

OTHER PUBLICATIONS

First Office Action dated Mar. 5, 2014 pertaining to Chinese Patent Application No. 201180038716.5.
Office Action dated Dec. 4, 2013 pertaining to Colombian Patent Application No. 12-219958.
Office Action dated Apr. 15, 2014 pertaining to Eurasian Patent Application No. 201270812/28.
Cully et al., "Beyond PTEN mutations: the PI3K pathway as an integrator of multiple inputs during tumorigenesis," Nature Rev., 6, 184-192 (2006).
Gajate, Consuelo et al. "Involvement of Raft Aggregates Enriched in Fas/CD95 Death-Inducing Signaling Complex in Antileukemic Action of Edelfosine in Jurkat Cells," PLoS One, vol. 4, issue 4, e5044, 1-10 (Apr. 2009).
Ohmichi M et al., "Mechanisms of platinum drug resistance," Trends Pharmacol Sci, 26:113-116 (2005).
Papetti et al., "Mechanisms of normal and tumor-derived angiogenesis," American Journal of Physiology—Cell Physiology, 282(5), C947 (2002).
Parker RJ, "Platinum-DNA adduct in head and neck cancer patients receiving cisplatin and carboplatin chemotherapy, International Journal of Oncology," 3:331 (1993).
Pasetto LM et al., "The development of platinum compounds and their possible combination," Crit Rev Oncol Hematol, 60:59-75 (2006).
Pierce et al., "Genome-wide analysis of barcoded S. cerevisiae gene-deletion mutants in pooled cultures," Nat Protocols (2007).
Rosenberg, B., "Platinum complex-DNA interatctions and anticancer activity," Biochemie, 1978, 60, 859-867.
Sedletska Y et al., "Cisplatin is a DNA-damaging antitumour compound triggering multifactorial biochemical responses in cancer cells: importance of apoptotic pathways," Curr Med Chem Anticancer Agents, 5:251-265 (2005).
Schellens JH et al., "Relationship between the exposure to cisplatin, DNA-adduct formation in leucocytes and tumor response in patients with solid tumors," Br J Cancer, 73:1569-1575 (1996).
Siddik ZH, "Cisplatin: mode of cytotoxic action and molecular basis of resistance, Oncongene," 22:7265-7279 (2003).
Slavin et al., "One- and Two- Dimensional 31P NMR Characterization of Pure Phosphato Chelates in Cytidine-5'-di-and -triphosphatoplatinum (II) complexes," J. Chem. Soc. Chem. Comm., 1256-1258 (1990).
Slavin et al., "Phosphonato Complexes of Platinum (II): Kinetics of Formation and Phosphorus-31 NMR Studies," J. Inorg. Biochem., 40, 339-347 (1990).
Sorenson CM et al., "Mechanism of cis-diamminedichloroplatinum(II)-induced cytotoxicity: role of G2 arrest and DNA double-strand breaks," Cancer Res, 48:4484-4488 (1988).
Stanko, J.A., results quoted by M. J. Cleare in "Platinum Coordination Complexes in Cancer Chemotherapy" (T. A. Connors and J. J. Roberts, Eds.), Springer-Verlag: New York, 1974; pp. 25-26.
Sulis et al., "PTEN: from pathology to biology," Trends Cell Biol, 13, 478-83 (2003).
Vaisman et al., "Cell Cycle Changes Associated With Formation of Pt-DNA Adducts in Human Ovarian Carcinoma Cells With Different Cisplatin Sensitivity," Cytometry 27:54-64 (1997).
Vleminckx et al., "Genetic manipulation of E-cadherin expression by epithelial tumour cells reveals an invasion suppressor role," Cell, 66, 107-119 (1991).
Wang et al., "Cellular Processing of Platinum Anticancer Drugs," Nature Reviews Drug Discovery, 4, 307-320 (Apr. 2005).
Wei SQ et al., "Role of ERK1/2 kinase in cisplatin-induced apoptosis in human ovarian carcinoma cells," Chin Med Sci J, 19:125-129 (2004).
Welters MJ et al., "Pharmacodynamics of cisplatin in human head and neck cancer correlation between platinum content, DNA adduct levels and drug sensitivity in vitro and in vivo," Br J Cancer, 79:82-88 (1999).
Wernyj RP et al., "Molecular mechanisms of platinum resistance: still searching for the Achilles' heel," Drug Resist Updat, 7:227-232 (2004).
Wesseling et al., "Angiogenesis in brain tumors; pathobiological and clinical aspects," J. Neurooncol., 32:253-265 (1997).
Wood FE et al., "195Pt and 31P nuclear magnetic resonance studies of the binding of the cis-Pt(NH3)2+2 moiety to phosphate in aqueous solution," Inorganica Chimica Acta, 67:L19 (1982).
Zhang et al., "Differential sensitivity of human glioblastoma LN18 (PTEN-positive) and A172 (PTEN-negative) cells to Taxol for apoptosis," Brain Res., 1239:216-225 (2008).
Notice of Allowance in U.S. Appl. No. 12/187,376 dated Nov. 19, 2009 (5 pages).
Office Action in U.S. Appl. No. 12/187,376, dated Aug. 26, 2009 (6 pages).
Notice of Allowance in U.S. Appl. No. 12/722,189, dated Aug. 26, 2011 (2 pages).
Notice of Allowance in U.S. Appl. No. 12/722,189, dated Aug. 5, 2011 (2 pages).
Notice of Allowance in U.S. Appl. No. 12/722,189, dated Jul. 21, 2011 (5 pages).
Office Action in U.S. Appl. No. 12/722,189, dated Jun. 10, 2011 (5 pages).
Office Action in U.S. Appl. No. 12/722,189, dated Oct. 5, 2010 (5 pages).
Notice of Allowance in U.S. Appl. No. 13/221,458, dated Apr. 4, 2013 (8 pages).
Notice of Allowance in U.S. Appl. No. 13/221,458, dated Aug. 15, 2012 (5 pages).
Office Action in U.S. Appl. No. 13/221,458, dated May 2, 2012 (5 pages).
Office Action in U.S. Appl. No. 13/221,458, dated Jun. 19, 2012 (5 pages).
Notice of Allowance in U.S. Appl. No. 13/842,885, dated Dec. 13, 2013.
Office Action in U.S. Appl. No. 13/842,885, dated Aug. 20, 2013.
Notice of Allowance in EP08797320.2, dated Oct. 9, 2013.
Office Action in in EP08797320.2, dated Apr. 3, 2012 (5 pages).
Examination Report in EP08797320.2, dated Aug. 22, 2011 (5 pages).
Office Action in CN200880101577.4, dated May 25, 2011 (with translation) (14 pages).
Examination Report dated Dec. 29, 2017 pertaining to Indian Patent Application No. 30/CHENP/2013.

* cited by examiner

PHOSPHAPLATIN COMPLEXES AND METHODS FOR TREATMENT OF PROLIFERATIVE DISEASES USING THE PHOSPHAPLATIN COMPLEXES

CROSS REFERENCE TO RELATED APPLICATIONS

This application is a divisional of U.S. patent application Ser. No. 13/701,313, filed Nov. 30, 2012, which is the national stage of International Application PCT/US2011/038948, filed Jun. 2, 2011, which International Application claims the benefit of priority to U.S. Provisional Application Ser. No. 61/351,514, filed Jun. 4, 2010. Each of the foregoing applications is incorporated by reference herein in its entirety.

FIELD OF THE INVENTION

The present application relates generally to pyrophosphato platinum complexes; methods of synthesis of the provided complexes; compositions comprising the provided complexes; and to methods of treating proliferative diseases using the provided complexes, compositions comprising the provided complexes, or combinations thereof.

BACKGROUND OF THE INVENTION

In the year 2008, over 12 million people worldwide were diagnosed with cancer and over 7 million people died from cancer. In fact, cancer is the leading cause of death in the developed world and the second leading cause of death in developing countries (second only to HIV/AIDS). Once a cancer is diagnosed, the prognosis of the patient depends greatly on factors such as whether the cancer was diagnosed at an early stage, whether the cancer has spread throughout the body, and whether the cancer is or has become resistant to known chemotherapeutic regimens.

The platinum-based anticancer drugs cisplatin, carboplatin, and oxaliplatin, are widely used for treating a variety of cancers such as ovarian cancer, testicular cancer, small-cell lung cancer, and colorectal cancer. These compounds may be used in combination with other therapeutic regimens, including radiation therapy, to treat an expanded array of cancers. Currently, over 600 clinical trials in adjuvant therapeutic modes utilizing platinum compounds underscore the potential of platinum compounds to effectively treat a wide variety of other cancers. For example, recent breakthrough research suggests that a diabetic drug, rosiglitazone, may be effectively used in combination with carboplatin to treat multiple forms of cancer. This has now added a new dimension to the ever-growing applications of platinum-based anticancer drugs, because most adjuvant therapies have been limited primarily to combinations of cancer or radiation drugs with other cancer drugs. Thus, there remains an ongoing need for new platinum-based anticancer drugs, as well as new applications for platinum-based anticancer drugs.

Conventional platinum chemotherapeutics such as cisplatin initiate apoptosis at the G2 phase of the cell cycle predominantly through transcription inhibition and through replication inhibition processes, especially at high doses. Covalent binding to DNA through the N7 sites of guanine and adenine bases, both by intra-strand and inter-strand modes, is believed to be the key molecular event in triggering a cascade of cellular responses leading to apoptosis (programmed cell death). Numerous challenges have been identified in understanding the complexity of the cellular and molecular metallo-biochemistry of cisplatin and the molecular mechanisms of cytotoxicity. Briefly, it has been noted that platinated DNA is at the heart of the initiation of cytotoxicity. The platinum-bound DNA is sequestered by high mobility proteins (HMG) from undergoing repairs by the nucleotide excision repair (NER) enzymes. Furthermore, these Platinum—DNA adducts are believed to activate the p53 transcription factor, to induce histone phosphorylation, and to trigger chromatin condensation.

Although platinum-based chemotherapeutics are widely used to treat cancers, their applications in large numbers of patients have been limited because of severe side effects such as nephrotoxicity, neurotoxicity, ototoxicity, myelosuppression, and acquired resistance to platinum-metal drugs. For example, a significant percentage of patients becomes resistant to cisplatin treatment. Although carboplatin reduces some toxicity over cisplatin, it does not alleviate the resistance. Currently, oxaliplatin is approved to treat colorectal cancer, but its resistance is largely unexplored.

The art lacks an understanding at the molecular level of the development of resistance to conventional platinum-based chemotherapeutics and ways to overcome such resistance. Although the understanding is incomplete, it is believed that the ability to repair DNA damage by excising bound platinum from DNA mostly contributes to the resistance mechanisms. Other mechanisms implicated in contributing to resistance include, reduced intracellular accumulations of cisplatin due to decreased uptake linked with the down-regulation of expression of the copper transport protein, CTR1; increased efflux due to overexpression of cMOAT, ATP7A, and ATP7B; impaired downregulation of pro-apoptotic genes and up-regulation of anti-apoptotic genes. On the other hand, up-regulation of CTR1 protein has been linked with increased ototoxicity. Alternation of MAPKs and deactivation of platinum by glutathione and other small molecules and proteins, especially metallothionine, have also been postulated as contributing factors towards resistance to platinum drugs. In light of the aforementioned, there is a need for ways to overcome resistance to platinum drugs, including development of drugs that are not susceptible to DNA repair mechanisms.

In various embodiments, U.S. Pat. No. 7,700,649 (Bose) and U.S. Ser. No. 12/722,189 (Bose) meet some of the needs in the art by disclosing synthetic routes and cancer treatment methods involving a new class of platinum complexes, namely pyrophosphato complexes having platinum(II) or platinum(IV) metal centers. The disclosed compounds and methods are part of a drug development strategy based on creating a class of platinum antitumor agents that do not covalently bind DNA, thereby nullifying DNA-repair based resistance. This strategy is a paradigm shift from conventional platinum drug development approaches, in which DNA binding is the central theme in developing more efficient platinum anticancer agents.

Among the pyrophosphato platinum complexes disclosed in U.S. Pat. No. 7,700,649 (Bose) and U.S. Ser. No. 12/722,189 (Bose) are racemic trans-($\pm$)-1,2-cyclohexanediamine (pyrophosphato) platinum(II) and racemic trans-($\pm$)-1,2-cyclohexanediamine-trans-dihydroxo(pyrophosphato) platinum(IV). Although these racemic complexes have been found efficacious for treatments of some cancers, a need still exists for improved drug development approaches, including but not limited to, improving efficaciousness of pyrophosphato platinum therapeutics, reducing toxicities of such therapeutics, and inhibiting cancer cell growth by improved targeting of genes engaged in killing cancer cells.

SUMMARY OF THE INVENTION

In various embodiments, the present application fulfills the foregoing needs by disclosing a drug development strategy based upon enantiopure and enantioenriched monomeric pyrophosphato platinum complexes. Thus, the present disclosure provides the most effective forms of pyrophosphato platinum complexes, as well as identifying target genes engaged in killing cancer cells and inhibiting cancer cell growth. The provided complexes are stable, show enhanced cytotoxicity, and greater effectiveness than conventional anticancer agents. This drug development strategy is also a paradigm shift from conventional platinum drug development approaches, wherein DNA binding remains the central theme.

Among the various embodiments, the present application provides isolated, monomeric ((cis or trans)-1,2-cyclohexanediamine)(dihydrogen pyrophosphato)platinum (II) and ((cis or trans)-1,2-cyclohexanediamine)-trans-dihydroxo(dihydrogen pyrophosphato)platinum (IV) complexes, wherein the complexes are enantiopure or comprise an enantiomeric excess of the cis-1,2-cyclohexanediamine-based complex or one of the two distinguishable trans-1,2-cyclohexanediamine-based complexes. Thus, the present disclosure provides platinum (II) and platinum (IV) complexes selected from (i) ((1R,2R)-1,2-cyclohexanediamine)(dihydrogen pyrophosphato)platinum (II) (referred to herein as "(1R,2R)-pyrodach-2"); (ii) ((1S,2S)-1,2-cyclohexanediamine)(dihydrogen pyrophosphato)platinum (II) (referred to herein as "(1S,2S)-pyrodach-2"); (iii) ((1R,2S)-1,2-cyclohexanediamine) (dihydrogen pyrophosphato)platinum (II) or ((1S,2R)-1,2-cyclohexanediamine) (dihydrogen pyrophosphato)platinum (II) (which are superimposable mirror-image compounds and are referred to collectively herein as "cis-pyrodach-2"); (iv) ((1R,2R)-1,2-cyclohexanediamine)-trans-dihydroxo(dihydrogen pyrophosphato)platinum (IV) (referred to herein as "(1R,2R)-pyrodach-4"); (v) ((1S,2S)-1,2-cyclohexanediamine)-trans-dihydroxo(dihydrogen pyrophosphato)platinum (IV) (referred to herein as "(1S,2S)-pyrodach-4"); and (vi) ((1R,2S)-1,2-cyclohexanediamine)-trans-dihydroxo(dihydrogen pyrophosphato)platinum (IV) or ((1S,2R)-1,2-cyclohexanediamine)-trans-dihydroxo(dihydrogen pyrophosphato)platinum (IV) (which are superimposable mirror-image compounds and are referred to collectively herein as "cis-pyrodach-4"); as well as pharmaceutically acceptable salts or solvates of any of (i)-(vi). Referring to the amino groups on the 1,2-cyclohexanediamine ligand, in the compounds (i), (ii), (iv), and (v), the (1R,2R) and (1S,2S) stereochemistries represent amino groups in trans configurations, whereas in compounds (iii) and (vi) (1R,2S) and (1S,2R) stereochemistries represent amino groups in cis configurations.

The present disclosure additionally provides, in some embodiments, compositions comprising a therapeutically effective amount of one or more of the provided complexes and at least one pharmaceutically acceptable ingredient such as a carrier, diluent, adjuvant, or vehicle.

In yet other embodiments, the present disclosure provides methods for treating one or more proliferative diseases by administering to a subject in need thereof a therapeutically effective amount of a composition comprising one or more of the provided complexes.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, in which:

DETAILED DESCRIPTION OF THE INVENTION

Figure 1:
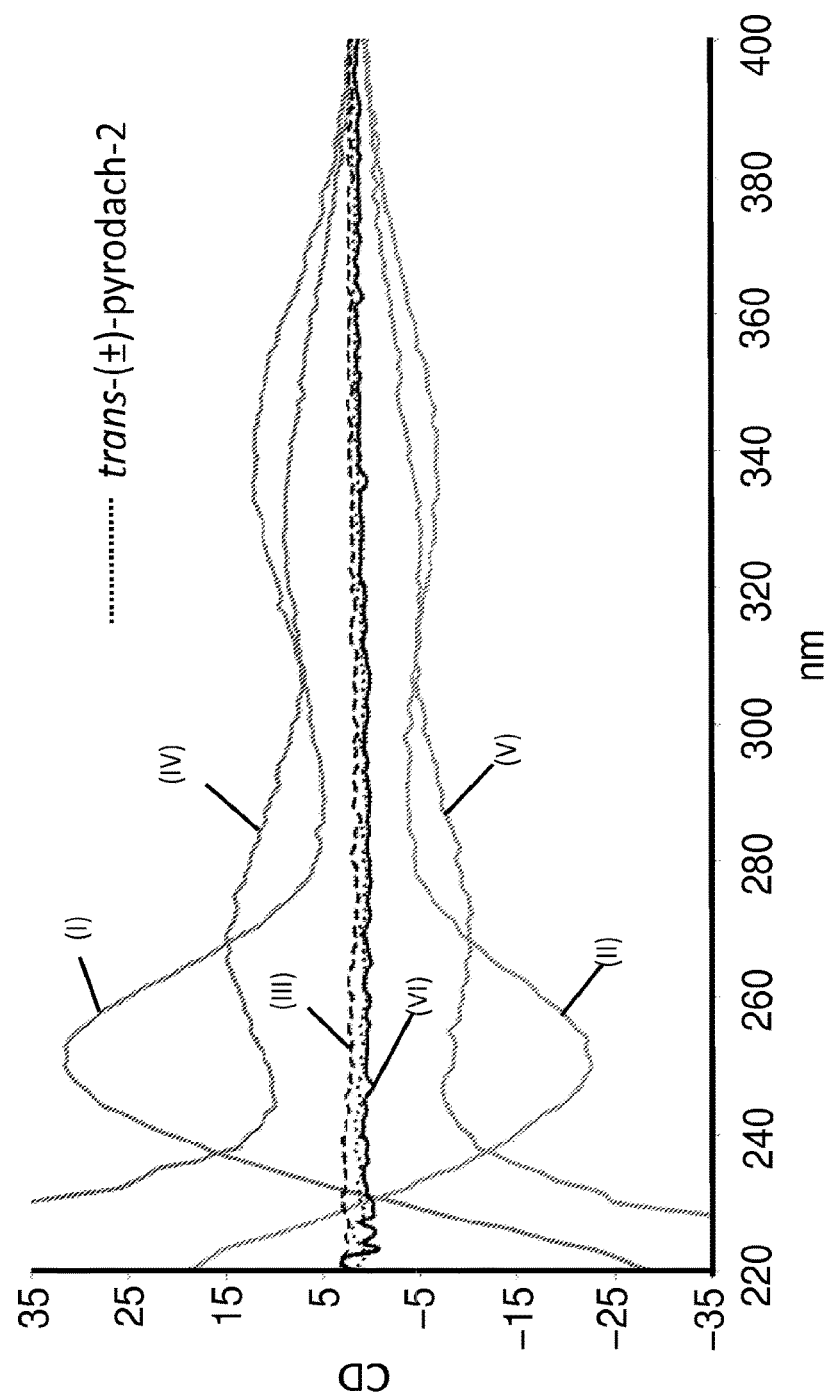
FIG. 1 shows circular dichroism spectra of stereoisomers of (I) (1R,2R)-pyrodach-2, (II) (1S,2S)-pyrodach-2, (III) cis-pyrodach-2, (IV) (1R,2R)-pyrodach-4, (V) (1S,2S)-pyrodach-4, (VI) cis-pyrodach-4, and trans-(±)-pyrodach-2.

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

Unless otherwise indicated, all numbers expressing quantities of ingredients, properties such as molecular weight, reaction conditions, and so forth as used in the specification and claims are to be understood as being modified in all instances by the term "about," which is intended to mean up to ±10% of an indicated value. Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

As used herein, the term "phosphaplatin" refers generally to platinum complexes coordinated with a single bidentate pyrophosphato ligand. Phosphaplatins according to embodiments described herein may have the following general structures (A) and (B):

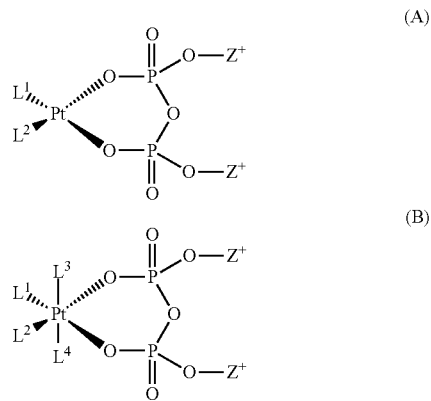

in which $L^1$ and $L^2$ represent neutral ligands (independently selected from $NH_3$; substituted or unsubstituted aliphatic amines; and substituted or unsubstituted aromatic amines), or a single bidentate neutral ligand (selected from substituted or unsubstituted aliphatic or aromatic diamines) with end groups $L^1$ and $L^2$, coordinated to the platinum metal center; $L^3$ and $L^4$ are ligands (selected from hydroxide, acetic acid, butyric acid, and alpha-hydroxy acids, amines or charged species thereof) coordinated to the platinum metal center. The pyrophosphato ligand may be neutral (not shown) or charged (shown). When charged, the pyrophosphato ligand is present with counterions, represented by $Z^+$. Examples of $Z^+$ include, without limitation, hydrogen; alkali metals such as sodium and potassium; and monovalent organic moieties. Preferably, $Z^+$ is a counterion that results in a pharmaceutically acceptable salt. Whether charged or neutral, the general structure of platinum(II) complexes represented by (A) is square-planar, and the general structure of platinum(IV) complexes represented by (B) is octahedral.

In general, phosphaplatins do not readily undergo hydrolysis, are soluble in aqueous solution at neutral pH, and are stable in aqueous solution at neutral pH. Furthermore, phosphaplatins show general cytotoxicity in cancer cell lines, and are effective in cell lines that are resistant to one or both cisplatin and carboplatin. Accordingly, phosphaplatins are effective, and in some cases more effective, in inducing cancer cell death as compared to known platinum cancer drugs, and exhibit desirable stability and solubility in solutions that are suitable for administration to patients. As used herein in reference to the phosphaplatins of the invention, "stable" refers to the resistance of the complexes to hydrolysis when maintained in aqueous solution at a pH in the range from 6-8 for a period of time from between 2 and six days.

Unlike cisplatin, carboplatin, and related platinum-based anti-cancer agents, phosphaplatins do not covalently bind DNA. Resistance to cisplatin, carboplatin, and related platinum anti-cancer agents is believed to originate from the efficient repair of DNA damage by a variety of enzymes including nuclear excision repair enzymes. However, because phosphaplatins do not covalently bind DNA, resistance towards phosphaplatins due to the DNA repair mechanism is unlikely. Data suggest that phosphaplatins trigger overexpression of fas and fas-related transcription factors, some proapoptotic genes such as Bak and Bax, and tumor suppression genes such as PUMA and PTEN. Moreover, phosphaplatins down-regulate BCL2, an antiapoptotic gene. Western Blot experiments that deal with protein expressions transcribed by these genes show the parallel trend. In addition, the cellular binding of phosphaplatins is less than cisplatin, yet phosphaplatins exhibit high cytotoxicity. Thus, the present invention provides effective platinum anticancer agents that have a different molecular target than those in the art.

The term "enantiomeric excess" is used herein according to its commonly understood definition. That is, for two enantiomers A and B that may be present in a mixture in molar amounts $M_A$ and $M_B$, respectively, the enantiomeric excess E of the enantiomer present in a higher molar amount in the mixture may be expressed by the relation % $E=|(M_A-M_B)/(M_A+M_B)\times100|$, where E>0%. A "racemic mixture" of the enantiomers A and B, which may be designated by abbreviations such as "rac" and/or "(±)" (or simply lack any reference to enantiomers) has E=0% because $M_A=M_B$. As a further illustration, a mixture consisting of A and B, in which $M_A=60\%$ and $M_B=40\%$, has an enantiomeric excess of A equal to 20%. The same mixture may be regarded in the alternative as a mixture consisting of 80% racemic mixture of A and B in combination with 20% enantiopure A, inasmuch as each molecule of B (40% of the mixture) may be paired with a molecule of A in the mixture (40% of the mixture) to leave unpaired an excess of molecules of A (20% of the mixture).

As used herein, the term "enantiopure" with regard to a molecule having two enantiomers, A and B, refers to a compound or composition containing substantially only one of the enantiomers A or B, but not both A and B. For an "enantiopure" complex, 97%≤E≤100%.

As used herein, the term "enantioenriched" refers, in its broadest sense, to a compound or composition containing a molecule having two enantiomers, A and B, such that the compound or composition has an enantiomeric excess of one of the enantiomers, either A or B. Thus, an "enantioenriched mixture of A and B" may refer to a mixture with an enantiomeric excess of A or to a mixture with an enantiomeric excess of B, wherein 0%<E≤100% for either A or B. As illustrative examples, the enantiomeric excess of either A or B may be greater than 0.01%, greater than 1%, greater than 10%, greater than 25%, greater than 50%, greater than 75%, greater than 90%, greater than 98%, greater than 99%, greater than 99.9%, or even equal to 100%.

In various embodiments, provided herein are stable, monomeric phosphaplatin complexes (and compositions comprising a therapeutically effective amount of one or more of said complexes). In some embodiments, said complexes and compositions may be used in methods of treating cancers, including but not limited to, cancers resistant to treatment by one or more of cisplatin, carboplatin, and oxaliplatin.

Complexes

In the various embodiments, provided are phosphaplatin complexes selected from the group consisting of:

(i) enantiopure (1R,2R)-pyrodach-2 having formula (I);

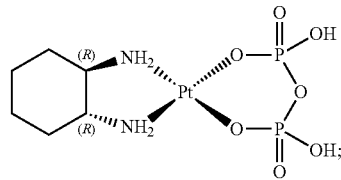

(ii) enantiopure (1S,2S)-pyrodach-2 having formula (II);

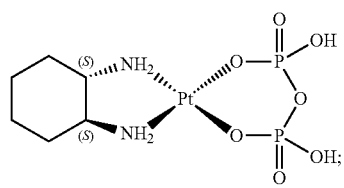

(iii) enantioenriched pyrodach-2 having an enantiomeric excess of either (1R,2R)-pyrodach-2 having formula (I) or (1S,2S)-pyrodach-2 having formula (II);

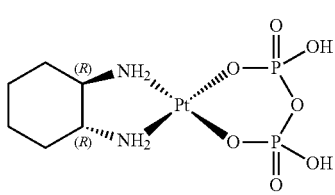

(iv) cis-pyrodach-2 having formula (III);

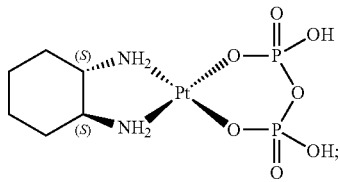

(v) enantiopure (1R,2R)-pyrodach-4 having formula (IV);

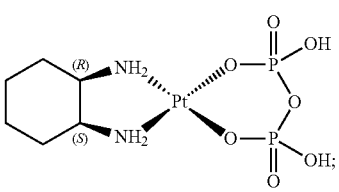

(vi) enantiopure (1S,2S)-pyrodach-4 having formula (V);

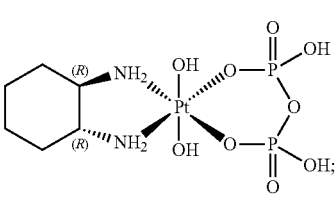

(vii) enantioenriched pyrodach-4 having an enantiomeric excess of either (1R,2R)-pyrodach-4 having formula (IV) or (1S,2S)-pyrodach-4 having formula (V); and

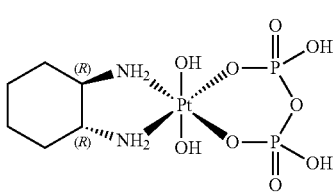

-continued

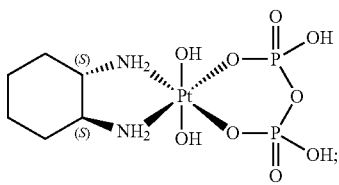

(viii) cis-pyrodach-4 having formula (VI)

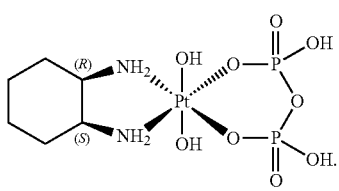

In the complexes according to formulas (I)-(VI), the shorthand notation "pyrodach" refers to a 1,2-cyclohexanediamine(pyrophosphato)platinum complex (where "pyro" refers to the bidentate pyrophosphato ligand and "dach" refers to the bidentate 1,2-cyclohexanediamine ligand (as named according to IUPAC conventions), known also as 1,2-diaminocyclohexane. The notation (1R,2R), (1S,2S), or cis before the term "pyrodach" refers to the sterochemical configuration of the chiral centers at the 1-position and the 2-position of the 1,2-cyclohexanediamine ligand. The number (i.e., 2 or 4) following the notation "pyrodach" refers to the oxidation number of the platinum center. That is "pyrodach-2" refers to a platinum(II) complex, and "pyrodach-4" refers to a platinum(IV) complex.

The phosphaplatins of formulas (I)-(VI), with platinum coordinated to pyrophosphate and 1,2-cyclohexanediamine ligands, can exist as four stereoisomers due to the possible cis- and trans-geometry of the two amino (—NH$_2$) groups at the chiral carbon centers 1 and 2 of the diamine ligand. These stereoisomers exhibit the (1R,2R)-, (1S,2S)-, (1R, 2S)-, and (1S,2R)-configurations. The trans-ligand, trans-1, 2-cyclohexanediamine, affords two enantiomers, having the (1R,2R)- and (1S,2S)-configurations, respectively. The cis-isomer in principle encompasses the (1R,2S)- and (1S,2R)-enantiomers, but these two cis-isomers are equivalent, superimposable mirror images indistinguishable from each other structurally and chemically. Thus, the two enantiomers of the cis-isomer will be referred to hereinafter simply as the "cis-isomer" and are referred to with a single formula.

The enantioenriched pyrodach-2 mixture (iii) and the enantioenriched pyrodach-4 mixture (vii) both are characterized by an enantiomeric excess greater than zero of either the (1R,2R)-enantiomer or the (1S,2S)-enantiomer. The enantiomeric excess may vary and in example embodiments may be greater than 0.01%, greater than 1%, greater than 10%, greater than 25%, greater than 50%, greater than 75%, greater than 90%, greater than 98%, greater than 99%, greater than 99.9%, or even equal to 100%. In example embodiments, the enantiomeric excess is of the (1R,2R)-enantiomer, for example, an enantiomeric excess of (1R, 2R)-enantiomer greater than 90%. In further example embodiments, the enantiomeric excess is of the (1S,2S)-enantiomer, for example, an enantiomeric excess of (1R, 2R)-enantiomer greater than 90%. In still further example embodiments, the enantioenriched pyrodach-2 mixture (i) and/or the enantioenriched pyrodach-4 mixture (ii) are enantiopure in either the (1R,2R)-enantiomer or the (1S,2S)-enantiomer.

In comparative data presented herein between the enantiopure complexes according to formulas (I), (II), (IV), and (V) and corresponding racemic mixtures disclosed in U.S. Pat. No. 7,700,649, hereinafter, a racemic mixture of (1R,2R)-pyrodach-2 and (1S,2S)-pyrodach-2 will be referred to by the shorthand notation "trans-(±)-pyrodach-2." Likewise, a racemic mixture of (1R,2R)-pyrodach-4 and (1S,2S)-pyrodach-4 will be referred to as "trans-(±)-pyrodach-4."

As a non-limiting example, the compounds of formulas (I)-(VI) may be synthesized from a starting material such as cis-(1,2-cyclohexanediamine) dichloroplatinum(II), which may be prepared by converting $K_2PtCl_4$ to $K_2PtI_4$ by the addition of potassium iodide. The $K_2PtI_4$ may then be reacted with a 1,2-cyclohexanediamine having a desired stereochemistry, such as cis-1,2-cyclohexanediamine, trans-(1R,2R)-1,2-cyclohexanediamine, trans-(1S,2S)-1,2-cyclohexanediamine, or mixtures thereof. The resulting (1,2-cyclohexanediamine)diiodoplatinum(II) complexes then may be transformed to the corresponding (1,2-cyclohexanediamine)diaquaplatinum(II) complexes in situ by adding two equivalents of silver nitrate. The diaqua species [Pt(1, 2-cyclohexanediamine)($H_2O$)$_2$] then may be converted to the cis-dichloro [Pt(1,2-cyclohexanediamine)Cl$_2$] complexes by addition of potassium chloride.

It will be understood that other suitable reaction conditions may be used. In non-limiting examples, the starting 1,2-cyclohexanediamine-platinum(II) complexes were reacted with excess pyrophosphate and the temperature may be from about 35° C. to about 45° C., or any preferred narrower range between 35° C. and 45° C. Good results have been obtained at 40° C. In some examples, the reaction may be allowed to proceed from about 13 hours to about 16 hours, or any preferred narrower range between 13 hours and 16 hours. Good results have been obtained at reaction times of 15 hours. In some examples, the pH can be from about 6 to about 7, from about 7 to about 8, and from about 8 to about 9. Good results have been obtained at pH of about 8.

The aqueous reaction mixture may be concentrated such that precipitates of pyrophosphate do not form. It will be understood that the aqueous reaction mixture may be concentrated in any suitable manner. For example, the aqueous reaction mixture may be concentrated by rotary evaporation.

Thereupon, the pH of the reaction mixture may be lowered rapidly to a pH of less than 2 by addition of a suitable acid. In some examples, nitric acid may be used to lower the pH. In some embodiments, the pH is in the range between about 1 to about 2. Good results have been obtained at pH of 1.

In some examples, the reaction mixture may be cooled to a temperature of between 5° C. and room temperature (25° C.±2° C.) after concentrating the reaction mixture. In other examples, the method also includes cooling the reaction mixture to a temperature of between 5° C. and room temperature after lowering the pH of the reaction mixture.

To prepare the platinum(IV) complexes according to formulas (II) and (V), additional steps are required to attach the hydroxo ligands. Thus, in addition to the steps described above, to the reaction mixture may be added hydrogen peroxide, and optionally a reagent selected from the group acetate salts, butyrate salts, and salts of alpha-hydroxy acids, after maintaining the reaction mixture at a temperature of about 30° C. to about 60° C. for a period of about 12 hours to about 18 hours at a pH from about 7 to about 9. The optional reagent that may be added together with hydrogen peroxide prior to concentration of the reaction mixture may be selected from sodium acetate, sodium butyrate, amines, and sodium salts of alpha-hydroxy acids. In other examples, the optional reagent added together with hydrogen peroxide prior to concentration of the reaction mixture may be selected from potassium acetate, potassium butyrate, any monodentate amines such as ammonia, isopropyl amine, and others, and potassium salts of alpha-hydroxy acids.

Compositions

In some of the various embodiments, additionally provided are compositions comprising one or more of (a) a provided phosphaplatin complex; (b) a pharmaceutically acceptable salt of (a); and (c) a pharmaceutically acceptable solvate of (a). Said compositions may additionally comprise at least one pharmaceutically acceptable ingredient selected from carriers, diluents, adjuvants, and vehicles, which generally refer to inert, non-toxic, solid or liquid fillers, diluents, or encapsulating materials unreactive with the phosphaplatins. These types of additives are well known in the art and are further described below with regard to treatment methods. According to the various embodiments, a provided composition comprises one or more of:

(i) enantiopure (1R,2R)-pyrodach-2 having formula (I), or pharmaceutically acceptable salt or solvate thereof;

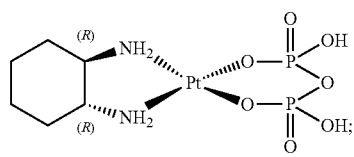

(ii) enantiopure (1S,2S)-pyrodach-2 having formula (II), or pharmaceutically acceptable salt or solvate thereof;

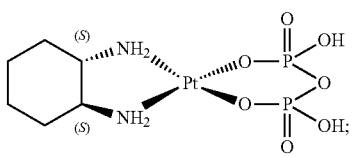

(iii) enantioenriched pyrodach-2 having an enantiomeric excess of either (1R,2R)-pyrodach-2 having formula (I) or (1S,2S)-pyrodach-2 having formula (II), or pharmaceutically acceptable salts or solvates thereof;

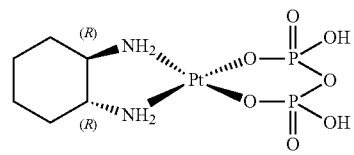

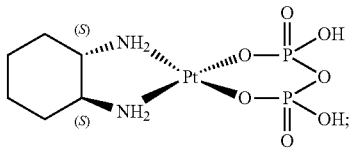

(iv) cis-pyrodach-2 having formula (III), or pharmaceutically acceptable salt or solvate thereof;

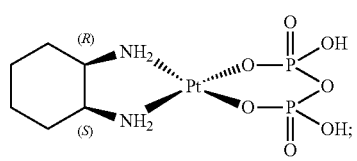

(v) enantiopure (1R,2R)-pyrodach-4 having formula (IV), or pharmaceutically acceptable salt or solvate thereof;

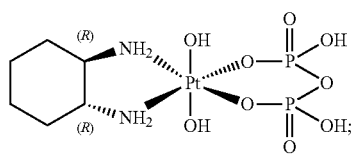

(vi) enantiopure (1S,2S)-pyrodach-4 having formula (V), or pharmaceutically acceptable salt or solvate thereof;

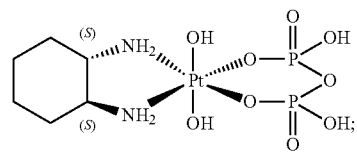

(vii) enantioenriched pyrodach-4 having an enantiomeric excess of either (1R,2R)-pyrodach-4 having formula (IV) or (1S,2S)-pyrodach-4 having formula (V), or pharmaceutically acceptable salts or solvates thereof;

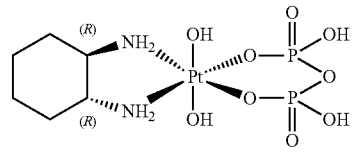

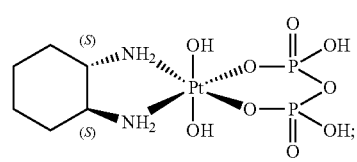

and (viii) cis-pyrodach-4 having formula (VI), or pharmaceutically acceptable salt or solvate thereof;

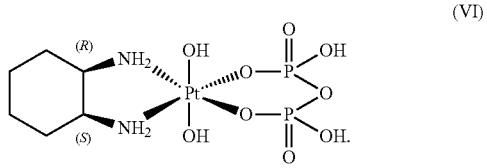

In some embodiments, a provided composition comprises one complex (or pharmaceutically acceptable salt or solvate thereof) having a formula according to any of formulas (I)-(VI). In some embodiments, a provided composition is a multicomplex mixture of at least two complexes (or pharmaceutically acceptable salts or solvates thereof) having formulas according to any of formulas (I)-(VI). The multicomplex mixture may comprise one, two, three, four, five, or six of the compounds according to formulas (I)-(VI), provided the multicomplex mixture is not a pure racemic mixture of (1R,2R)-pyrodach-2 and (1S,2S)-pyrodach-2 or a pure racemic mixture of (1R,2R)-pyrodach-4 and (1S,2S)-pyrodach-4.

Contemplated Methods

In still further embodiments, the complexes, compositions, or both, described above may be used alone, or with other pharmaceutically acceptable ingredients, in methods of treating proliferative diseases or disorders (collectively, "diseases"). The provided methods comprise administering to a subject in need thereof a therapeutically effective amount of a complex or composition described above. The subject may be an animal such as, for example, a mammal, including a human. Proliferative diseases contemplated to be treatable in humans include ovarian cancer, testicular cancer, small-cell lung cancer, non-small-cell lung cancer and head-and-neck cancers, skin cancer, pancreatic cancer, breast cancer, colon cancer, glioblastoma cancer. In some embodiments, it is contemplated that the complexes and/or compositions may be used in combination therapies involving concurrent or sequential treatment with known platinum-metal drugs such as cisplatin, carboplatin, and/or oxaliplatin. It is further contemplated that the complexes and/or compositions may be used to treat cancers resistant to treatment by one or more of cisplatin, carboplatin, oxaliplatin and/or used in combination with other treatment classes, including anti-mitotics such as taxanes, nucleoside analogs such as Gemcitabine, anthracycline antibiotics such as Doxorubicin, or targeted therapies such as monoclonal antibodies.

As described herein, the complexes of formulas (I)-(VI) have been shown to be as effective as, or more effective than, cisplatin and carboplatin, thus providing a method of cancer treatment for patients who previously lacked effective alternatives to cisplatin and carboplatin treatment. However, a patient need not have previously been treated with cisplatin or carboplatin to be treated with the provided complexes, compositions, and methods described herein. Administration of the treatment can be performed in a hospital or other medical facility by medical personnel.

The complexes of formulas (I)-(VI) may be administered and dosed in accordance with good medical practice, taking into account the clinical condition of the individual patient, the site and method of administration, scheduling of administration, patient age, sex, body weight and other factors known to medical practitioners. The pharmaceutically "therapeutic effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art. It is contemplated that the complexes of the present invention may be administered to animals, including mammals and humans alone or as compositions. Moreover, it is contemplated that the complexes of formulas (I)-(VI) may be administered over an especially wide therapeutic window. As one illustrative example, it is contemplated that one or more provided complexes may be administered in one or more doses of from 5 mg/kg to 50 mg/kg; alternatively from 10 mg/kg to 50 mg/kg; alternatively from 20 mg/kg to 50 mg/kg; alternatively from 30 mg/kg to 50 mg/kg; alternatively from 40 mg/kg to 50 mg/kg; alternatively from 45 mg/kg to 50 mg/kg. Of course, one of skill in the art will appreciate that therapeutic dosages may vary by complex administered, composition administered, and subject receiving the administered complex or composition. Thus, therapeutic doses greater than 50 mg/kg are also contemplated, as are therapeutic doses less than 5 mg/kg. The doses can be single doses or multiple doses over a period of several days. As an illustrative example, it is contemplated that the complexes of formulas (I)-(VI) may be administered in one, two, three, four, five, six, or more doses in one more days. It is also contemplated that the complexes may be administered continuously over one or more days, such as by a pump or drip. As another illustrative example, it is contemplated that the complexes may be administered for one, two, three, four, five, six, seven, eight, nine, ten, or more days.

In a method of treatment, the complexes of formulas (I)-(VI) can be administered in various ways. It should be noted that they can be administered as the complex and can be administered alone in aqueous solution taking advantage of the excellent solubility of these complexes, or as an active ingredient in combination with pharmaceutically acceptable carriers, diluents, adjuvants and vehicles. It is contemplated that the complexes can be administered orally, subcutaneously or parenterally including intravenous, intraarterial, intramuscular, intraperitoneally, intratonsillar, and intranasal administration as well as intrathecal and infusion techniques. Implants of the complexes may also be useful.

When the complexes of formulas (I)-(VI) are administered parenterally, they generally will be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for the compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. However, any vehicle, diluent, or additive used would have to be compatible with the phosphaplatin complexes.

Sterile injectable solutions can be prepared by incorporating the phosphaplatin complexes in the required amount of the appropriate solvent with one or more of the other ingredients, as desired.

A pharmacological formulation comprising the phosphaplatins can be administered to the patient in an injectable formulation containing any compatible carrier, such as various vehicle, adjuvants, additives, and diluents; or the phosphaplatin complexes can be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

EXAMPLES

The described embodiments will be better understood by reference to the following examples, which are offered by way of illustration and which one skilled in the art will recognize are not meant to be limiting.

Example 1

Synthesis of (1R,2R)-pyrodach-2 [formula (I)]

As a starting material for forming a platinum(II) complex, cis-diiodo- or cis-dichloro-(trans-(1R,2R)-(−)-1,2-cyclohexanediamine)platinum(II) was formed by reacting $K_2PtI_4$ or, more preferably $K_2PtCl_4$, respectively with (1R,2R)-(−)-1,2-cyclohexanediamine. The cis-diiodo-((1R,2R)-(−)-1,2-cyclohexanediamine)platinum(II) or, preferably, the cis-dichloro-((1R,2R)-(−)-1,2-cyclohexanediamine)platinum(II) then was dissolved with sodium pyrophosphate decahydrate in distilled water, pH 8, and the resultant mixture is incubated at 40° C. for 15 hours. Following the incubation period, the solution was concentrated by rotary evaporation and was filtered to remove any unreacted starting material. Rapidly lowering the pH to approximately 1.0 by addition of 1-N nitric acid precipitated the product. The precipitation was completed by cooling at about 0° C., and the product was isolated by vacuum filtration and washed with cold water and acetone. The synthesis yielded enantiopure (1R,2R)-pyrodach-2.

Example 2

Synthesis of (1S,2S)-pyrodach-2 [formula (II)]

Enantiopure (1S,2S)-1,2-cyclohexanediamine(pyrophosphato) platinum(II) was prepared in a manner analogous to the method described in Synthesis Example 1, except that cis-diiodo- or cis-dichloro-(trans-(1S,2S)-(+)-1,2-cyclohexanediamine) platinum(II) was used as a starting material in the place of cis-diiodo- or cis-dichloro-(trans-(1R,2R)-(−)-1,2-cyclohexanediamine) platinum(II), respectively. The synthesis yielded enantiopure (1S,2S)-pyrodach-2.

Example 3

Synthesis of (1R,2R)-pyrodach-4 [formula (IV)]

The starting material from Synthesis Example 1, i.e., cis-diiodo- or cis-dichloro-(trans-(1R,2R)-(−)-1,2-cyclohexanediamine) platinum(II) and sodium pyrophosphate decahydrate was dissolved in distilled water, pH 8, and the resultant mixture was incubated at 40° C. for 15 hours. Following the incubation period, an aliquot of 30% $H_2O_2$ was added to the reaction mixture, and the reaction mixture was allowed to react for an additional 3 hours. The solution then was concentrated by rotary evaporation and was filtered to remove any unreacted starting material. Rapidly lowering the pH to approximately 1.0 by addition of 1-N nitric acid precipitated the product. Precipitation was completed by cooling at about 0° C., and the product was isolated by vacuum filtration and washed with cold water and acetone. The synthesis yielded enantiopure (1R,2R)-pyrodach-4.

Example 4

Synthesis of (1S,2S)-pyrodach-4 [formula (V)]

Enantiopure (1S,2S)-1,2-cyclohexanediamine-trans-dihydroxo(pyrophosphato) platinum(IV) was prepared in a manner analogous to the method described in Synthesis Example 3, except that the starting material from Synthesis Example 2, i.e., cis-diiodo- or cis-dichloro-(trans-(1S,2S)-(+)-1,2-cyclohexanediamine) platinum(II) was used as a starting material in the place of cis-diiodo- or cis-dichloro-(trans-(1R,2R)-(−)-1,2-cyclohexanediamine) platinum(II), respectively. The synthesis yielded enantiopure (1S,2S)-pyrodach-4.

Example 5

Synthesis of cis-pyrodach-2 [formula (III)]

In a 500-mL round-bottom flask provided with a stirring bar, sodium pyrophosphate decahydrate (0.400 g) was dissolved in distilled water (250 mL). The pH of the solution then was adjusted to 8.0 using 2-M nitric acid. Then the solution was placed in a water bath at 40° C. and stirred with the magnetic bar. Then to the stirring solution, cis-dichloro-(cis-1,2-cyclohexanediamine)platinum(II) (0.100 g, 0.26 mmol) was added. The mixture was allowed to react for 15 hours, and then the solvent was evaporated at 48° C. under vacuum to a volume of 5 mL. Then the mixture was passed through filter paper and the solution was collected in a 10-mL vial provided with a stirring bar. The vial was placed in an ice bath over a stirring plate and with gentle stirring the pH was adjusted from an initial 6.5 to 2.0 using 2-N nitric acid. Once the lower pH was reached, a precipitate slowly developed. The stirring was continued for an additional 5 minutes, after which the suspension was filtered through a medium-porosity fritted-glass filter that has been kept in ice before its use. Then the solid was washed with cold water (2 portions of 5 mL) and cold acetone (2 portions of 5 mL), and the filter was left in a desiccator overnight. This produced a light yellow powder (0.077 g, 0.16 mmol, 60% yield).

Example 6

Synthesis of cis-pyrodach-4 [formula (VI)]

In a 500-mL round-bottom flask provided with a stirring bar, sodium pyrophosphate decahydrate (0.400 g) was dissolved in distilled water (250 mL). The pH of the solution was then adjusted to 8.0 using 2 M nitric acid. Then the solution was placed in a water bath at 40° C. and was stirred with the magnetic bar. To the stirring solution cis-dichloro-(cis-1,2-cyclohexanediamine) platinum(II) (0.100 g, 0.26 mmol) was added. The mixture was allowed to react for 15 hours, 3 mL of 30% (w/w) $H_2O_2$ were added, and three additional hours of reaction time were given. Then the solvent was evaporated at 48° C. under vacuum to a volume of 5 mL. Then the mixture was passed through filter paper, and the solution was collected in a 10-mL vial provided with a stirring bar. The vial was placed in an ice bath over a stirring plate and was gently stirred while the pH was adjusted from an initial 6.5 to 2.5 using 2-N nitric acid. Soon after the lower pH was reached, a precipitate slowly developed. The stirring was continued for an additional 5 minutes, and then the suspension was filtered through a medium-porosity fritted-glass filter that had been kept in ice before its use. The solid was washed with cold water (2 portions of 5 mL) and cold acetone (2 portions of 5 mL) and the filter was left in a desiccator overnight. This produced a white powder (0.120 g, 0.23 mmol, 88% yield).

Example 7

Characterizations of the Phosphaplatins

All phosphaplatins synthesized according to the above Synthesis Examples exhibit solubility greater than 40 mM/L in aqueous solution at neutral pH in PBS and bicarbonate buffer. (1R,2R)-pyrodach-2 and (1R,2R)-pyrodach-4, in particular, show remarkable stability at neutral pH in aqueous solution. Typically, no decomposition is observed within seven days after dissolving the phosphaplatin compounds in water and observing by $^{31}$P-NMR spectroscopy.

Compounds prepared according to the Synthesis Examples above were characterized by circular dichroism (CD) spectroscopy to verify isomeric configuration, and by $^{31}$P-NMR and Mass Spectrometry to verify the composition. An additional CD spectra was run on a trans-(±)-pyrodach-2 racemic mixture prepared according to the methods described in U.S. Pat. No. 7,700,649.

The CD spectra were recorded in phosphate buffer (50 mM) at pH 6.8. The (1R,2R)- and the (1S,2S)-forms of both pyrodach-2 and pyrodach-4 showed optical activities attributable chirality, but the racemic mixture (trans-(±)-pyrodach-2) and the cis-isomers of both pyrodach-2 and pyrodach-4 did not exhibit any CD peaks.

The CD spectra are depicted in FIG. 1, in which the numbers in parentheses refer to the compound of the formula corresponding to the number in the parentheses. The concentrations of the compounds as analyzed were: (I), 2.7 mM; (II), 2.5 mM; (III), 1.3 mM; (IV), 3.5 mM; (V), 2.9 mM; (VI), 2.7 mM; and trans-(±)-pyrodach-2, 3.5 mM.

Example 8

In Vitro Efficacy and Cell Survival Assay (Clonogenic Assay)

To determine the relative activities of the phosphaplatins of formulas (I)-(VI), each stereoisomer was tested through in vitro clonogenic assays using human ovarian cancer cells, human colon cancer cells, and human head-and-neck cancer cells. Human ovarian cancer cells, A2780 and A2780/C30 (cross resistant to 30 μM cisplatin and 100 μM carboplatin), were obtained from Dr. Thomas Hamilton (Fox Chase Cancer Center, Philadelphia, Pa.). Cells were cultured on monolayer using RPMI 1640 supplemented with 10% fetal bovine serum, 2 mM glutamine, 0.25 units/mL insulin and penicillin/streptomycin (100 units/mL) in a 37° C. incubator continuously gassed with 5% $CO_2$. Cells were subcultured using 0.0625% trypsin in HBSS to maintain cells in exponential cell growth.

Half-maximal inhibitory concentration ($IC_{50}$) values were determined using a clonogenic assay or a CyQUANT® cell proliferation assay. In the clonogenic assay, for example, 500-700 A2780 cells from a single cell suspension were plated onto 60 mm petri plates 24 hours before treatment with the platinum compounds to permit cell attachment. On the day of treatment with the platinum compounds described in the above Synthesis Examples, the medium was decanted and was replaced with the appropriate concentration of phosphaplatin compounds (from 50 nM to 75 μM) at three different time points, and the treated cells were placed back into the 37° C. incubator for 24 hours. Triplicate plates were set up for each platinum compound concentration. After the 24-hour treatment, the medium containing the platinum compounds was decanted and was replaced with fresh medium. These plates were returned to the 37° C. incubator for 7 days for colony formation.

In the CyQUANT cell proliferation assay, the $IC_{50}$ values were determined by measuring the DNA content using a CyQUANT® Cell Proliferation Assay Kit (Invitrogen), which contains a green-fluorescent dye that exhibits strong fluorescence intensity when bound to cellular DNA. In these experiments, desired number of cells were exposed to phosphaplatins of different concentrations for 72 hr. before measuring the DNA content. Because the DNA content is proportional to the number of surviving cells, the assay provides a quantitative measure of proliferating cells. The technique is described in detail in Jones et al., "Sensitive determination of cell number using the CyQUANT cell proliferation assay," *J. Immunol. Methods*, vol. 254, pp. 85-98 (2001).

The $IC_{50}$ data from clonogenic assays and/or CyQUANT cell proliferation assays are summarized in TABLES 1-5. In TABLES 1-5, except where actual error values are given, each reported value is assumed to have an error not greater than ±15% of the reported value; and unless otherwise specified, the data were obtained from clonogenic assays.

TABLE 1

IC$_{50}$ values for phosphaplatin compounds on human ovarian cancer cell lines:
A2780, epithelial human ovarian cancer; and A2780/C30, epithelial human
ovarian cancer resistant to 30 μM cisplatin and 100 μM carboplatin

| | IC$_{50}$ (μM) for various cell lines at various treatment times | | | | | |
|---|---|---|---|---|---|---|
| | A2780 | | | A2780/C30 | | |
| Compound | 1 hour | 24 hours | 7 days | 1 hour | 24 hours | 7 days |
| (1R,2R)-pyrodach-2 (I) | | 1.0 ± 0.1 | 0.5 ± 0.1 | | 6.3 | 1.1 ± 0.1 |
| (1S,2S)-pyrodach-2 (II) | | 1.1 ± 0.1 | | | | |
| trans-(±)-pyrodach-2 (comparative) | 22 ± 4 | 2.4 ± 0.2 | | 48 ± 5 | | |
| (1R,2R)-pyrodach-4 (IV) | 45 ± 5 | 13 | 4.9 | | 11 ± 2 | 11.7 |
| (1S,2S)-pyrodach-4 (V) | | 5.2 | | | | |
| trans-(±)-pyrodach-4 (comparative) | 170 ± 20 | | | 155 ± 20 | | |
| cis-pyrodach-2 (III) | | 0.3 ± 0.05 | | | | |
| cis-pyrodach-4 (VI) | | 3.8 | | | | |
| cisplatin (comparative) | 7 | | | 100 | | |
| carboplatin (comparative) | 90 | | | >200 | | |

TABLE 2

IC$_{50}$ values for phosphaplatin compounds on human ovarian cancer
cell lines: OVCAR-10, human ovarian cancer resistant to cisplatin
treatment; and OVCAR-5, advanced human ovarian cancer cells

| | IC$_{50}$ (μM) for various Human Ovarian Cancer Cell Lines at various treatment times | | | |
|---|---|---|---|---|
| | OVCAR-10 | | OVCAR-5 | |
| Compound | 24 hours | 48 hours | 24 hours | 48 hours |
| (1R,2R)-pyrodach-2 (I) | 0.42 | | | 15.4 |
| (1S,2S)-pyrodach-2 (II) | | 6.9 | | 4.5 |
| trans-(±)-pyrodach-2 (comparative) | 4.6 | | 12.2 | |
| (1R,2R)-pyrodach-4 (IV) | 10.2 | | 19.8 | |
| (1S,2S)-pyrodach-4 (V) | | | | 5.6 |
| trans-(±)-pyrodach-4 (comparative) | 14.4 | | | |
| cisplatin (comparative) | 4.1 | | | |
| carboplatin (comparative) | 26.7 | | | |

TABLE 3

IC$_{50}$ values for phosphaplatin compounds on human head-and-
neck cancer cell lines: USMCC10b, human head-and-neck
cancer cell line; and UMSCC-10b/15s, cisplatin-resistant
human head-and-neck cancer cell line

| | IC$_{50}$ (μM) 7-day treatment | |
|---|---|---|
| Compound | UMSCC10b | UMSCC10b/15s |
| (1R,2R)-pyrodach-2 (I) | 1.6 | 2.1 ± 0.2 |
| (1S,2S)-pyrodach-2 (II) | 1.1 | |
| trans-(±)-pyrodach-2 (comparative) | | 5.0 |
| (1R,2R)-pyrodach-4 (IV) | 1.7 | 3.9 |

TABLE 4

IC$_{50}$ values for phosphaplatin compounds
on human colon cancer cell lines (HT-29)

| | IC$_{50}$ (μM) at various treatment times | | IC$_{50}$ (μM) (CyQUANT) |
|---|---|---|---|
| Compound | 24 hours | 7 days | 72 hours |
| (1S,2S)-pyrodach-2 (II) | | | 10 |
| (1R,2R)-pyrodach-2 (I) | 9.6 | 2.1 | 2.7 |
| (1R,2R)-pyrodach-4 (IV) | 23 | | |
| cisplatin (comparative) | | | 6.5 |

TABLE 5

IC$_{50}$ values for phosphaplatin compounds on human cancer cell lines: A459, human lung adenocarcinoma cancer cells; U251, human glioblastoma cancer cells; PC-3, human metastatic colon cancer cells; SKMEL-2, human skin melanoma cancer cells; MCF-7, human breast cancer cells; OVCAR-8, human ovarian cancer cells with dysfunctional p53; and OVCAR-10, human ovarian cancer resistant to cisplatin treatment, all determined by CyQUANT technology, described above, that directly measures DNA content by measuring fluorescence signals of intercalations

| Compound | IC$_{50}$ (µM) for various Human Cancer Cell Lines (72-hour treatment time) | | | | | | |
|---|---|---|---|---|---|---|---|
| | A549 | U251 | PC-3 | SKMEL-2 | MCF-7 | OVCAR-8 | OVCAR-10 |
| (1R,2R)-pyrodach-2 (I) | 0.9 | 4.6 | 1.7 | 19.7 | 2.3 | 1.2 | 0.8 |
| (1S,2S)-pyrodach-2 (II) | 11.9 | 24 | 10.7 | 10 | 11.2 | 13.5 | 5.9 |
| trans-(±)-pyrodach-2 (comparative) | 11.1 | 10.1 | 24.5 | 8.3 | | 9.4 | 11.8 |
| (1R,2R)-pyrodach-4 (IV) | 6.3 | 3.9 | 20.5 | 34 | | 11.4 | 17.8 |
| (1S,2S)-pyrodach-4 (V) | 21 | 10 | 19.1 | 4.7 | | 15.1 | 35.8 |
| trans-(±)-pyrodach-4 (comparative) | 12.2 | 14.6 | 20 | 14.6 | | 12.3 | 23.2 |
| cisplatin (comparative) | 2.8 | 0.75 | 1.08 | 5.34 | 5.1 | 6.3 | 3.1 |

Additionally these isomeric compounds were also tested by exposing them for 144 hours in the following cell lines: UMSCC10b, Panc-1, UMSCC15s, A2780/C30 and HCC1806. The isomer (1R,2R)-pyrodach-2 exhibited surprisingly superior activity when compared to racemic trans-(±)-pyrodach-2. For example, (1R,2R)-pyrodach-2 exhibited an IC$_{50}$ value of 1.7 (µM) compared to an IC$_{50}$ value of 18.5 (µM) for racemic trans-(±)-pyrodach-2 in pancreatic cell line Panc-1; (1R,2R)-pyrodach-2 exhibited an IC$_{50}$ value of 0.3 (µM) compared to an IC$_{50}$ value of 8.9 (µM) for racemic trans-(±)-pyrodach-2 in head and neck cancer cell line UMSCC10b; and (1R,2R)-pyrodach-2 exhibited an IC$_{50}$ value of 9.7 (µM) compared to an IC$_{50}$ value of >30 (µM) for racemic trans-(±)-pyrodach-2 in breast cancer cell line HCC1806.

Among the trans-isomers, clonogenic assays indicated far superior activity of the (1R,2R)-pyrodach-2 and (1R,2R)-pyrodach-4 isomers over the racemic mixtures trans-(±)-pyrodach-2 and trans-(±)-pyrodach-4, respectively. For example, the IC$_{50}$ value was found to be 180±15 µM when the trans-(±)-pyrodach-4 was exposed to human ovarian cancer cells (A2780) for an hour; whereas the IC$_{50}$ for the same cell line was found to be 40±10 µM for (1R,2R)-pyrodach-4 under otherwise identical experimental conditions (Table 1). Extended exposures of (1R,2R)-isomers to a variety of human cancer cell lines yielded much lower IC$_{50}$ values, indicating potentials of these compounds as effective anticancer drugs. For example, (1R,2R)-pyrodach-2 has an IC$_{50}$ value of 500 nM (0.5 µM) from the clonogenic assay for human ovarian cell and 2 µM for the resistant human head and neck cancer.

Both enantiopure (1R,2R)-pyrodach-2 and (1S,2S)-pyrodach-2 compounds show equal activity within experimental error when A2780 cells were exposed for at least 24 hr. But when cells are exposed for shorter period of time, e.g., 1 hour, differential activities between the (1R,2R)- and the (1S,2S)-forms were observed. The (1R,2R)-forms show superior activity compared to the (1S,2S)-isomer at shorter time exposure, indicating faster uptake of the (1R,2R)-isomer by the cells. Higher IC$_{50}$ values for the racemic forms compared to either the (1R,2R)- or the (1S,2S)-form may indicate self-association of the two forms which perhaps are taken by the cells at a reduced rate.

For de novo cisplatin-resistant human ovarian cancer (OVCAR-10), (1R,2R)-pyrodach-2 exhibited better in vitro efficacy than (1S,2S)-pyrodach-2. Noteworthy is that (1R,2R)-pyrodach-2 exhibited remarkably superior activity over cisplatin in human ovarian cancer cell lines OVCAR-10 (TABLES 2 and 5) and OVCAR-8 (TABLE 5).

The cis-isomer exhibited superior activity against human ovarian cancer (A2780) compared to the other compounds. For example, cis-pyrodach-2 and cis-pyrodach-4 show IC$_{50}$ values 300 nM and 4 µM, respectively, after exposure to A2780 cells for 24 hours, compared with 1.0 µM and 18 µM, respectively, for the corresponding (1R,2R)-pyrodach-2 or (1R,2R)-pyrodach-4 forms. Note that cisplatin and carboplatin yielded much higher IC$_{50}$ values, i.e., 5.0 µM and >60 µM respectively under identical conditions.

Without intent to be bound or limited by theory, the anticipated chemical principle teaches that the IC$_{50}$ value of the racemic forms should be equal to the arithmetic average of the respective IC$_{50}$ values of the (1R,2R)-isomer and the (1S,2S)-isomer. However, as shown in the tables above, the IC$_{50}$ value of racemic form (for example, of pyrodach-2 in A2780) is much higher than expected based on a 50/50 mixture of (1R,2R)-enantiomer and (1S,2S)-enantiomer. These data suggest that racemic forms are less potent than expected, based on enantiomeric distribution, for unknown reasons. One plausible explanation might be that racemic forms self-associate and, thereby, are not effectively taken by the cells.

Figure 2:
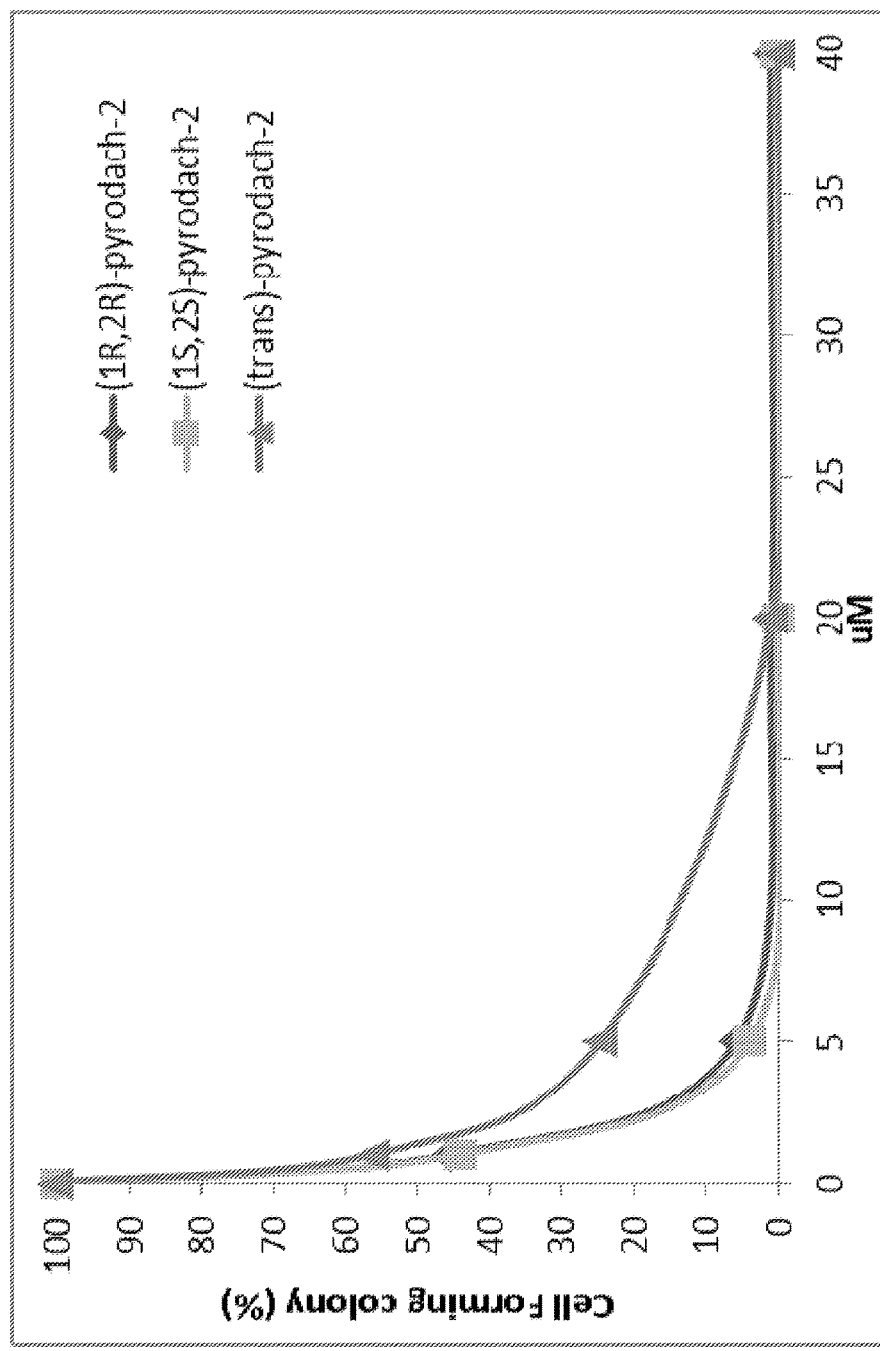
FIG. 2 depicts activities of (1R,2R)-pyrodach-2, (1S,2S)-pyrodach-2, and trans-(±)-pyrodach-2 as determined from clonogenic assays by exposing human ovarian cancer cells (A2780) to various concentrations of compounds for 24 hours.
Figure 3:
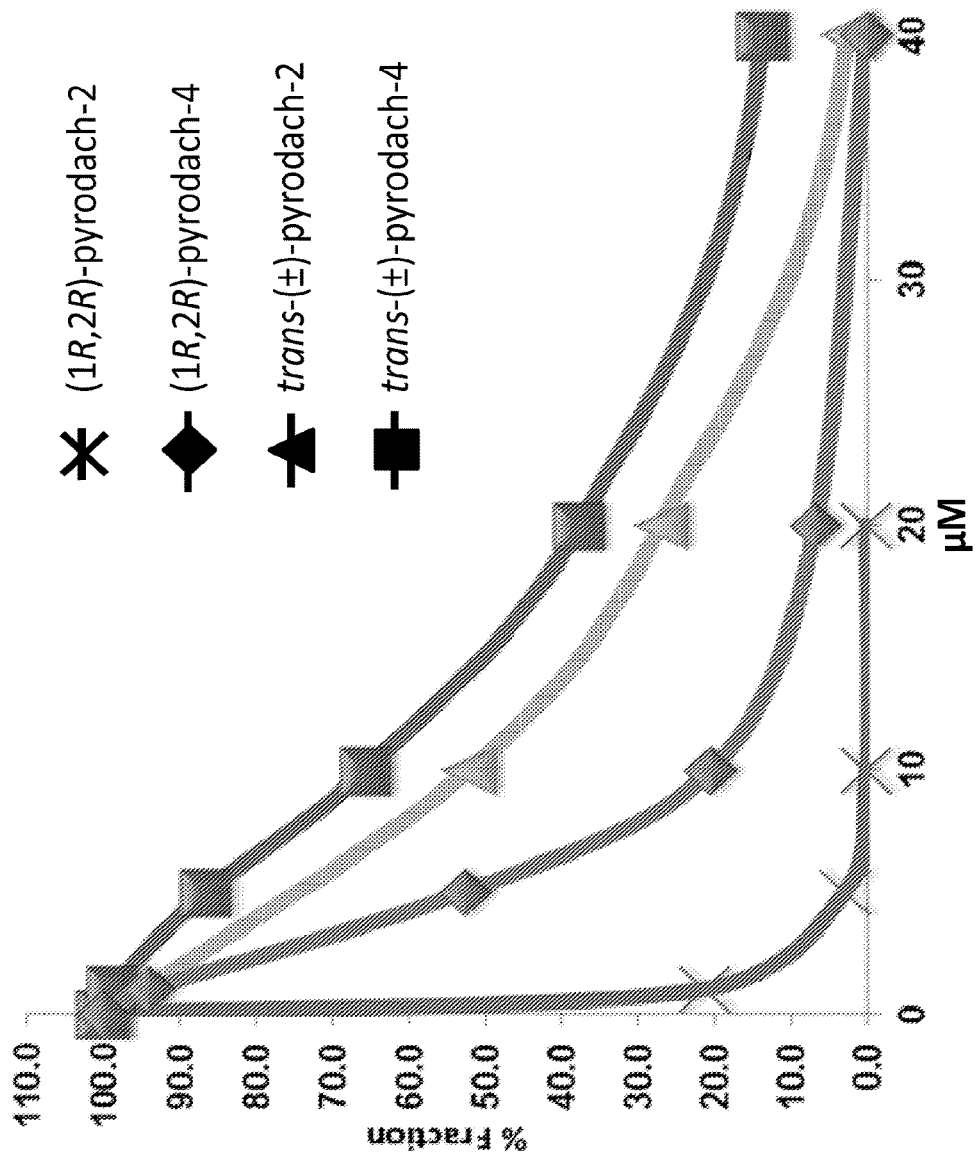
FIG. 3 depicts activities of (1R,2R)-pyrodach-2, (1S,2S)-pyrodach-2, and trans-(±)-pyrodach-2 as determined from clonogenic assays by exposing cisplatin-resistant human ovarian cancer cells (OVCAR-10) to various concentrations of compounds for 24 hours.

In further tests, cells were treated with the platinum compounds continuously for 7 days. Colonies were fixed and stained using 2% crystal violet in 4% formaldehyde. Colonies containing more than 50 cells were scored. The number of scored colonies from the triplicate plates was averaged, and this number was divided by the number of cells plated to obtain a value for the fraction of cells forming colonies. These values for fraction of cells forming colonies then were corrected for plating efficiency by dividing the fraction by the number of cells forming colonies in plates that were not treated with platinum compounds. The data for colony formation with A2780 are shown in FIG. 2. Note that both the (1R,2R)-pyrodach-2 and the (1S,2S)-pyrodach-2 enantiomers yield almost identical IC$_{50}$ values of 1.0±0.1 µM for the (1R,2R) and of 1.1±0.1 µM for the (1S,2S), whereas the racemic mixture yielded much higher IC$_{50}$ value of 2.4±0.2 µM indicative of lower efficacy of the racemic mixture. Similar data for OVCAR-10 are shown in FIG. 3, comparing (1R,2R)-pyrodach-2 (RD2), (1R,2R)-pyrodach-4 (RD4), trans-(±)-pyrodach-2 (T-D2), and trans-(±)-pyrodach-4 (T-D4).

Clinical studies have shown that the (1R,2R)-enantiomer of oxaliplatin, with reference the same 1,2-diaminocylohexane carrier ligand in oxaliplatin as is present in the phosphaplatins described herein, exhibits superior efficacy over the other stereoisomers of oxaliplatin. In contrast to oxaliplatin, all three pyrophosphato isomers (i.e., (1R,2R)-, (1S,2S)-, and cis) of both pyrodach-2 and pyrodach-4 are very active against a variety of cancers. There appears to be no universal trend, however. For example, as detailed above, (1R,2R)-pyrodach-2 and (1S,2S)-pyrodach-2 showed almost equal $IC_{50}$ values in human A2780 cancer cells when these compounds were exposed to the cells for 24 hours, whereas for de novo cisplatin-resistant human ovarian cancer (OVCAR 10), the (1R,2R)-pyrodach-2 exhibited better in vitro efficacy. On the other hand, (1S,2S)-pyrodach-4 showed superior activity over (1R,2R)-pyrodach-4 in all human ovarian cancer cells. The cis-isomers of pyrodach-2 and pyrodach-4 exhibited superior activity against human ovarian cancer (A2780) compared to the trans-isomers. Thus, the data reveal as a whole that some specific cancers can be treated with specific isomers at lower doses compared to racemic forms by avoiding toxicity from other isomers that would be present in the racemic forms.

Example 9

Monitoring of Fas Overpression by Immunofluorescence

A six-well plate with loose, pretreated cover slips was seeded with human ovarian cancer cells, A2780 and A2780/C30 (cross resistant to 30 µM cisplatin and 100 µM carboplatin), obtained from Dr. Thomas Hamilton (Fox Chase Cancer Center, Philadelphia, Pa.) in 2.5 mL of media. Cells were cultured as a monolayer using RPMI 1640 supplemented with 10% fetal bovine serum, 2 mM glutamine, 0.25 units/mL insulin and penicillin/streptomycin (100 units/mL) (Fisher Scientific, Pittsburg, Pa.) in a 37° C. incubator continuously gassed with 5% $CO_2$.

The cells at 70% confluency were treated with one of the phosphaplatin compounds from the above Synthesis Examples for 1 hour. The plates then were carefully washed twice with ice-cold phosphate-buffered saline (PBS), were replaced with regular media, and were incubated for an additional 1 hour at 37° C. with 5% $CO_2$. The cover slips were washed with PBS twice, and the cells were treated with freshly prepared 1% formaldehyde and then incubated at room temperature for 5 to 7 minutes. The fixed cells were washed with PBS for three times and were blocked with 2% FBS/PBS at 4° C. for 30 minutes, followed by washing the cells with PBS three times for 5 minutes each wash.

Individual cover slips were removed and flipped over onto 100 µL of a 1:100 dilution of FAS primary antibody (Cell Signaling Technology Inc., Danvers, Mass.) in 5% BSA/1% milk/PBS on a Parafilm® surface for 1 hour at room temperature. Thereupon, the cover slips were transferred back to a clean six-well plate for each subsequent wash, namely three washes with PBS, each for 5 minutes. The cover slips were flipped over a second time on another clean Parafilm® surface and were incubated with 100 µL of secondary FITC-antibody at a 1:500 dilution in 5% BSA/1% milk/PBS for 1 hour at room temperature. The cover slips then were washed with PBS three times at 5 minutes each. The moist cover slips then were mounted onto a microscope slide with Ultracruz® mounting media with DAPI (4',6-diamidino-2-phenylindole) (Santa Cruz Biotechnology, Santa Cruz, Calif.) for identifying the cell nuclei. Microscopy was performed using a fluorescence microscope at 10×, 40×, and 100× magnifications.

Example 10

Western Blot/Immunodecoration for Protein Expression

Following 12% SDS-PAGE electrophoresis, proteins were transferred to a PVDF membrane using 100 V for 1.5 hours at 4° C. Membranes were washed with 0.05% TWEEN-20 and Tris-buffered saline (TBST) solution and blocked with 5% non-fat dry milk and 1% BSA. The membrane was incubated with a 1:25,000 dilution of primary antibody of the protein of interest over night at 4° C. Membranes were washed with 0.05% TBST followed by incubating in the corresponding HRP-conjugated antibody (1:40,000 dilution). The proteins were visualized using ECL-Advance chemiluminescent system (Amersham-GE Healthcare Biosciences, Pittsburg, Pa.).

The phosphaplatins activate a number of proapototic and tumor suppression genes such as FAS, PTEN, PUMA, BAX and others. Experiments through Western Blots confirm high levels of protein expressions transcribed by these genes. For example, trans-(±)-pyrodach-4 treated mice exhibit upregulation of FAS (up to 25-fold), BAX (up to 4 fold), PUMA (up to 5-fold), and down regulation of VEGFR (up to 50%) upon exposure of trans-(±)-pyrodach-4 for 1 hour to 12 hours. Likewise, BCL2 was down regulated as much as 70% by RR-pyrodach-2 and RR-pyrodach-4. Additionally, FAS, FADD, and platinum compound were co-localized in the lipid rafts. These activations are also associated with the increased expression of Sphingomyelinase (Smase), as verified by the increased protein expression of SMase.

Smase hydrolyzes sphingomyelin to ceramide and phosphoryl choline. In a typical experiment, cancer cells ($1 \times 10^6$) are exposed to (1R,2R)-pyrodach-2 or (1R,2R)-pyrodach-4 (10 µM) at different time intervals (from 5 min to 2 hr). Cells are centrifuged and cell lysate is collected and washed with cold PBS. Amplex red reagent kit (Invitrogen) is used to monitor the Smase activity. The assays are performed based on the recommended protocols included with the kit. Typically, 11 µL of cell lysate is suspended in 50 mM sodium citrate buffer (pH 5.0) on a 96-well plate, and sphingomyelin (5.0 mM) is added to each well. Samples are incubated for 1 hour at 37° C. Following the incubation, 100 µL of Amplex Red reaction solution containing 100 mM Tris-HCl (100 µM), Amplex Red (2 unit/mL) horseradish peroxidase, 0.2 unit/mL choline oxidase, and 8 unit/mL alkaline phosphatase (pH 8.0), are added to each well. Samples are then incubated for 30 minutes at 37° C. Fluorescence intensity is measured at 590 nm using an excitation wavelength of from 530 nm to 560 nm. Fluorescence values from wells containing control samples (untreated) are subtracted from each sample measurement.

Example 11

Determination of Platinum in the Lipid Raft

Platinum content was quantitatively measured on a Graphite Furnace Atomic Absorption Spectrometer (Perkin Elmer AA-600) from calibration curves established by using a platinum standard (Perkin Elmer, Waltham, Mass.) in 0.1% HNO$_3$. The treated phosphaplatin cells were washed with 1 mL of ice-cold PBS and halt protease inhibitor, PI (Pierce, Rockford, Ill.) 4 times and the pellet was collected by centrifugation at 4° C. at 1000×g between each wash. The cell pellets were brought up in 250 µL of PBS/PI, and protein content was measured by using the micro BCA method (Pierce, Rockford, Ill.). Bovine serum albumin (BSA) prepared at different concentrations was used to plot the standard curve. Quantified protein samples were digested in concentrated HNO$_3$ for 4 hours, followed by treatment with 30% H$_2$O$_2$ for 1 hour prior to analysis.

Example 12

Toxicity Studies in SCID Mice

Female SCID mice from 4 to 5 weeks old (c.b-17/LCR-Prkdc(SCID)/Crl, Strain Code 236′, Charles River Labs, Wilmington, Mass.) were acclimated for one week before initiation of toxicity trials. Via sterile 26-gauge needles and syringes, the mice were injected intra-peritoneally (i/p) with 100 µL of one of the phosphaplatin compounds described in the above Synthesis Examples in sterile filtered PBS. The injections ranged in dosage from 5 mg/kg to 60 mg/kg and occurred once on day 1, once on day 3, and once on day 5.

To evaluate the toxicity of the phosphaplatin compounds, adverse events (i.e., >20% weight loss and/or change in food consumption, departure from normal behavior, other health issues, or death) were recorded every day. Frequency and severity of occurrence of the adverse events in the mice injected with the phosphaplatin compounds was compared to the same in control groups of mice. The control groups were given a mock injection (as a control for stress response) or an injection consisting of PBS (vehicle).

Two groups of mice were treated with commercially available platinum compounds for comparison, with the dosage based on previously published data (i.e., cisplatin at 12 mg/kg and carboplatin at 60 mg/kg) as comparison with phosphaplatin compounds. At the end of the study, all mice were anesthetized with 358 mg/kg avertin and blood was collected by cardiac puncture using a 26-gauge needle and a tubercuilin syringe. Thereby, the mice were euthanized by exsanguination under anesthesia. After euthanasia organs including the liver, spleen, heart, lung, ovary, and kidney were harvested, stored in 10% Formalin, and paraffin blocked for histopathological examination. Changes in tissue characteristics were examined by a skilled pathologist.

Ovarian tumor inflicted SCID mice were treated with trans-(±)-pyrodach-2 and trans-(±)-pyrodach-4 at various doses up to 40 mg/kg, and tumor growth was monitored up to six weeks or until the tumor size became so large that these animals were sacrificed. The tumor growth or regression by the phosphaplatin-treated mice was then compared with cisplatin-treated mice (7 mg/kg) and carboplatin-treated mice (60 mg/kg). Three doses of platinum compounds were administered on alternate days when the tumor grew to a size of at least 100 mm$^3$ size. Gross and net log cell kill values were then calculated using the formulas:

$$\text{Gross Log cell Kill} = ((T - C))/(3.32Td)$$

$$\text{Net Log cell Kill} = \frac{(T - C - \text{duration of the treatment})}{3.32Td}$$

where T and C are median times in days to grow tumor to a specified size, and Td is the median time in days to double the size of the tumor in control animals.

The gross log cell kill values recorded for three dose-regimen was found to be greater than 3 and the log net cell kill value was greater than 2 at a dose of 40 mg/kg. In contrast, cisplatin (7 mg/kg) treated mice, although showing tumor regression, died within 7 days. Carboplatin treated mice (60 mg/kg dose) displayed much lower log cell kill values (less than 2) compared to trans-(±)-pyrodach-4. Further escalation of carboplatin dose was not possible, because more than 50% of the population had died at the 60 mg/kg dose. Based on the in vitro data, it is believed that cis-pyrodach-2, cis-pyrodach-4, (1R,2R)-pyrodach-2, and (1R,2R)-pyrodach-4 in particular would exhibit better efficacy than the racemic trans-(±)-pyrodach-4.

Example 13

In Vivo Efficacy on Ovarian Cancer Cell Line A2780

Stable clonal ovarian cancer cell lines A2780 were grown in cell culture until 80-90% confluency was reached. Trypsin (GIBCO/BRL, Grand Island, N.Y.) was used to detach adherent cells. Trypsinized cells were thoroughly washed with PBS (Phosphate Buffered Saline) to remove trypsin. Efficacy of phosphaplatin compounds were evaluated using human ovarian cancer, A2780 by subcutaneous xenograft in SCID Hairless OutBred, SHO-Prkdc$^{scid}$Hr$^{hr}$, (Charles River Labs, Wilmington, Mass.) mice. Female SCID mice 4 to 5 weeks old were acclimated for one week before initiation of efficacy trials.

Cancer cells were re-suspended in PBS, and all mice except for negative control mice were injected subcutaneously with from 1×10$^6$ cells/0.10 mL to 5×10$^6$ cells/0.10 mL in PBS and were evaluated for tumors as a function of time using sterile 26 gauge needles and syringes. The mice were examined daily for tumor growth. Tumors were measured using digital calipers. The tumor volume was calculated by the formula (W$^2$×L)/2, where W is the tumor measurement at the widest point, and L is the tumor dimension at the longest point, where the volume of the tumor in mm$^3$ is equivalent to the weight in mg.

After approximately 2 weeks of the subcutaneous injection of cancer cells, the tumors that had reached a distinguishable tumor sizes (approximately 100-200 mm$^3$), phosphaplatin compound administration or control injections were initiated. The mice were administered phosphaplatin compounds intra-peritoneally once on day 1, again once on day 3, and again once on day 5. Each group of xenograft mice was treated with phosphaplatin compounds, and a matched set was treated with vehicle/placebo (PBS solution) and mock injection (as a control for stress response). In addition, two groups of mice were treated with commercially available platinum compounds for comparison with the phosphaplatin compounds, with dosages of the commercially available platinum compounds being based on previously published data (i.e., cisplatin at 12 mg/kg and carboplatin at 60 mg/kg).

The xenograft SCID mice were monitored every day for any adverse events in their health by measuring weight loss/gain and food consumption. Measurements were stopped and the study was ended when the tumor size exceeded 3000 mm$^3$. At the end of the study, mice were anesthetized with 358 mg/kg avertin, and blood was collected by cardiac puncture using a 26-gauge needle and a tubercuilin syringe. Thereby, the mice were euthanized by exsanguination under anesthesia. After euthanasia organs including the liver, spleen, heart, lung, ovary, and kidney were harvested, stored in 10% Formalin, and paraffin blocked for histopathological examination. Changes in tissue characteristics were examined by a skilled pathologist.

Figure 4:
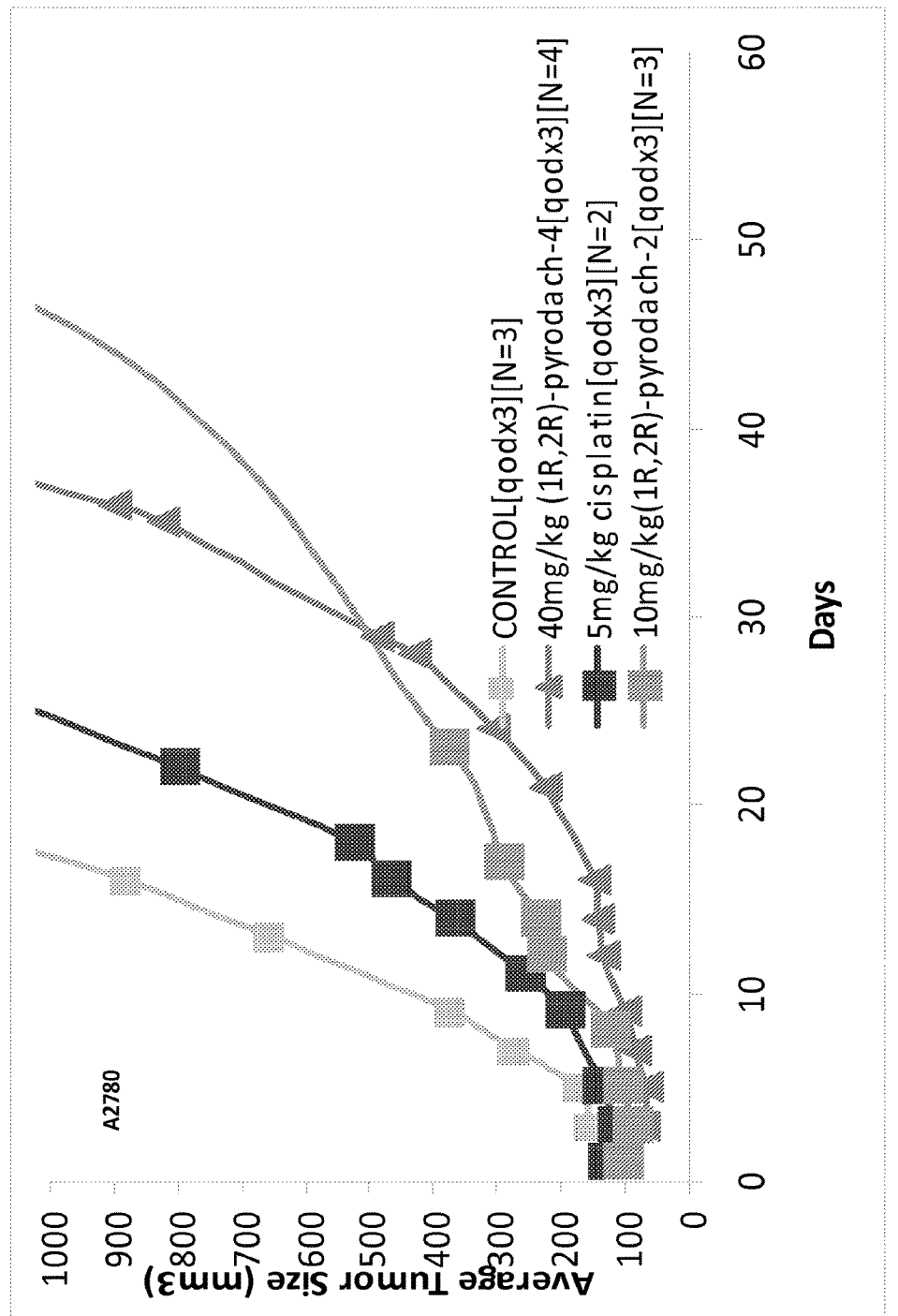
FIG. 4 is a plot of average tumor size over a period of six weeks during administration of phosphaplatins according to embodiments disclosed herein, on human ovarian cancer cells in mice.

Efficacy data of (1R,2R)-pyrodach-2 and (1R,2R)-pyrodach-4 against human ovarian cancer A2780 in the mouse xenograft model (immunocompromised NIH III mice) are summarized in FIG. 4. During the trial, mice were treated every other day for three days ("qodx3")—once on day 1, once on day 3, and once on day 5. In particular, mice were treated with 40 mg/kg of (1R,2R)-pyrodach-2, 10 mg/kg of (1R,2R)-pyrodach-4, or of 5 mg/kg cisplatin. The numbers N in the legend of FIG. 4 report the number of trials, over which the shown data points were derived as averages. The data in FIG. 4 from the first ten days of treatments with (1R,2R)-pyrodach-2 and (1R,2R)-pyrodach-4 clearly show a tumor regression of during initial stages of the treatment.

Example 14

In Vivo Efficacy on Human Ovarian Cancer and Human Head-and-Neck Cancer

Human Ovarian cancer (OVCAR-10) is known to exhibit resistant to both cisplatin and carboplatin. Stable human clonal ovarian cancer cell lines OVCAR-10 and head and neck cancer UMSCC10b were grown separately in cell culture until 80-90% confluency was reached. Trypsin (GIBCO/BRL, Grand Island, N.Y.) was used to detach adherent cells. Trypsinized cells were thoroughly washed with PBS (Phosphate Buffered Saline) to remove trypsin. Efficacy of phosphaplatin compounds were evaluated by subcutaneously implanting human OVCAR-10 and UMSCC-10b xenograft in SCID Hairless OutBred, SHO-Prkdc$^{scid}$Hr$^{hr}$, (Charles River Labs, Wilmington, Mass.) mice, NIH (NIH III: NIHBNX-F; NIHS-Lystbg Foxn1nu Btkxid, 4-week old female, Taconic(Rensselaer, N.Y.) mice.

Female SCID/NIH mice 4-5 weeks old were acclimated for one week before initiation of efficacy trials. Cancer cells were re-suspended in PBS and all mice except for negative control mice were injected subcutaneously with from $1\times10^6$ cells/0.10 mL to $5\times10^6$ cells/0.10 mL in PBS. The tumor size was evaluated as a function of time. The mice were examined daily for tumor growth. Tumors were measured using digital calipers. The tumor volume was calculated by the formula $(W^2\times L)/2$, where W is the tumor measurement at the widest point, and L is the tumor dimension at the longest point, where the volume of the tumor in mm$^3$ is equivalent to the weight in mg.

After approximately 2 weeks of the subcutaneous injection of cancer cells, the tumors that had reached a distinguishable tumor sizes (approximately 100 mm$^3$ to 200 mm$^3$), phosphaplatin compounds of desired doses were administred intra-peritoneally. These administrations were done one time on day 1, once on day 3, and once on day 5.

Each group of xenograft mice was treated with phosphaplatin compounds, and a matched set was treated with vehicle/placebo (PBS solution) and mock injection (as a control for stress response). In addition, two groups of mice were treated with commercially available platinum compounds for comparison with the phosphaplatin compounds, with dosages of the commercially available platinum compounds being based on previously published data (i.e., cisplatin at 12 mg/kg and carboplatin at 60 mg/kg). The xenograft SCID mice/NIH were monitored every day for any adverse events in their health by measuring weight loss/gain and food consumption. Measurements were stopped and the study was ended when the tumor size exceeded 3000 mm$^3$.

At the end of the study, mice were anesthetized with 358 mg/kg avertin, and blood was collected by cardiac puncture using a 26-gauge needle and a tubercuilin syringe. The mice were euthanized by exsanguination under anesthesia. After euthanasia organs including the liver, spleen, heart, lung, ovary, and kidney were harvested, were stored in 10% Formalin, and were paraffin blocked for histopathological examination. Changes in tissue characteristics were examined by a skilled pathologist.

Figure 5:
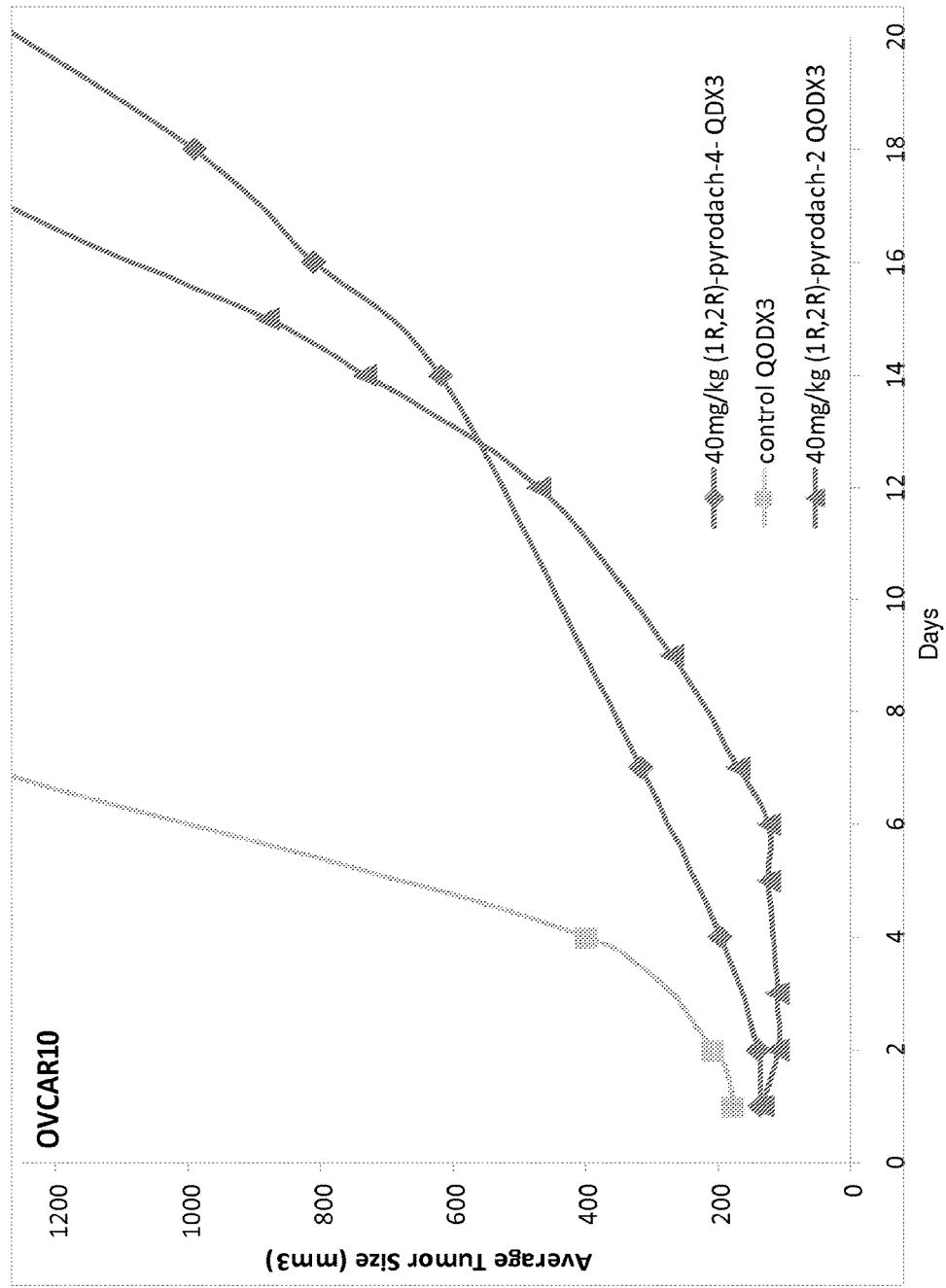
FIG. 5 shows efficacies of (1R,2R)-pyrodach-2 and (1R,2R)-pyrodach-4, described in detail below, against cisplatin-resistant human ovarian cancer cells (OVCAR-10)
Figure 6:
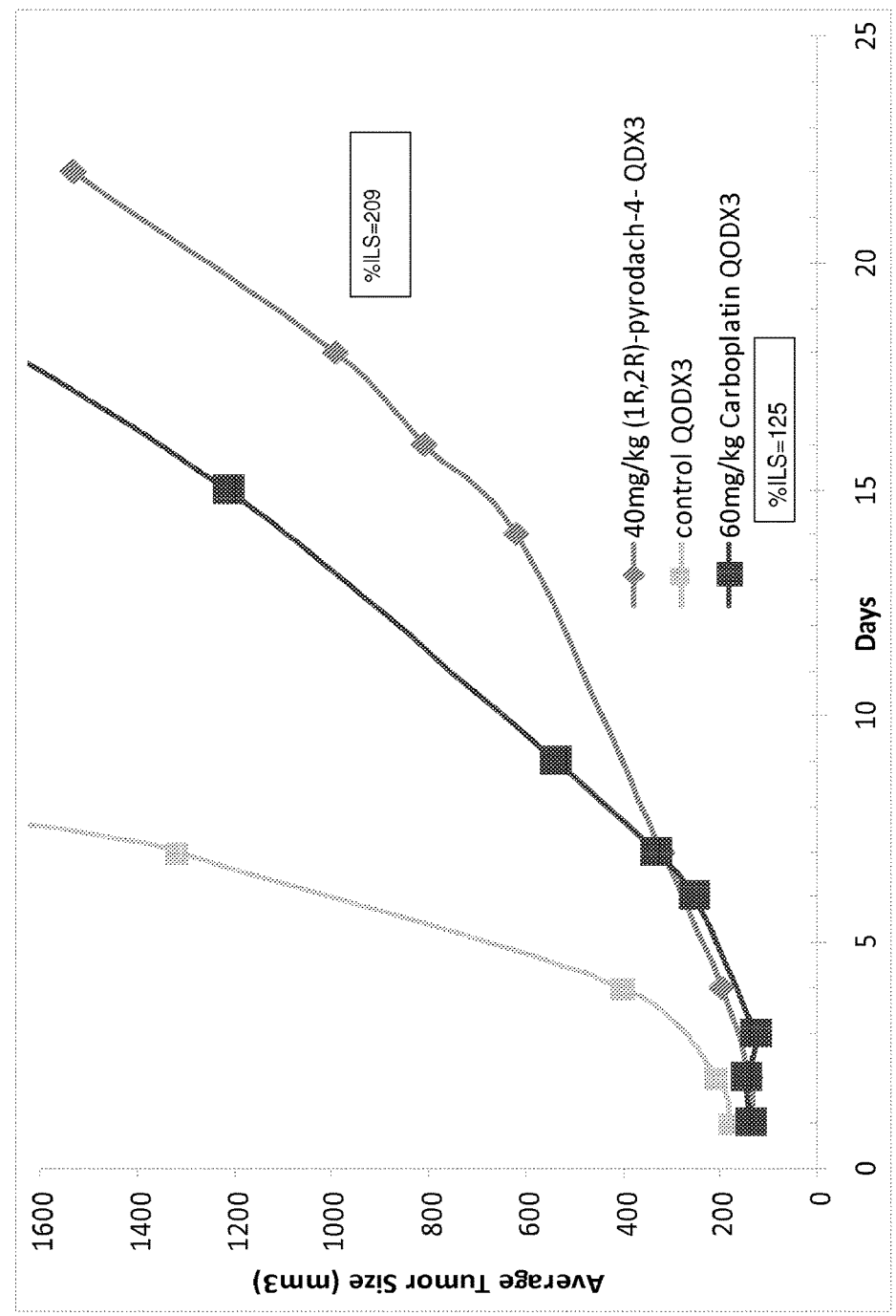
FIG. 6 shows plots of tumor size over time, comparing a control (PBS/Bic) administered once every other day for three days ("qodx3"), carboplatin dosed at 60 mg/kg (administered qodx3) and (1R,2R)-pyrodach-4 dosed at 40 mg/kg [administered once every day for three consecutive days ("qdx3")]

Efficacy data of (1R,2R)-pyrodach-2 and (1R,2R)-pyrodach-4 against human ovarian cancer cells OVCAR-10 are summarized in FIG. 5, compared with a PBS/Bicarb control. Doses were administered (40 mg/kg body weight) when the tumor reached 100-200 mm$^3$ in size. The treated mice showed tumor regression during the treatment time. Measurements of tumor sizes over time are summarized in FIG. 6 for a control (PBS/Bicarbonate) administered qodx3, carboplatin at 60 mg/kg administered qodx3, and (1R,2R)-pyrodach-4 at 40 mg/kg administered qdx3. Dotted arrows emphasize the time (in days, interpolated as necessary) at which average tumor size reached 1000 mm$^3$. Compared with the control, whereas carboplatin exhibited a percent increased life-span (% ILS) of only about 125%, the (1R,2R)-pyrodach-4 exhibited % ILS of about 209%.

Figure 7:
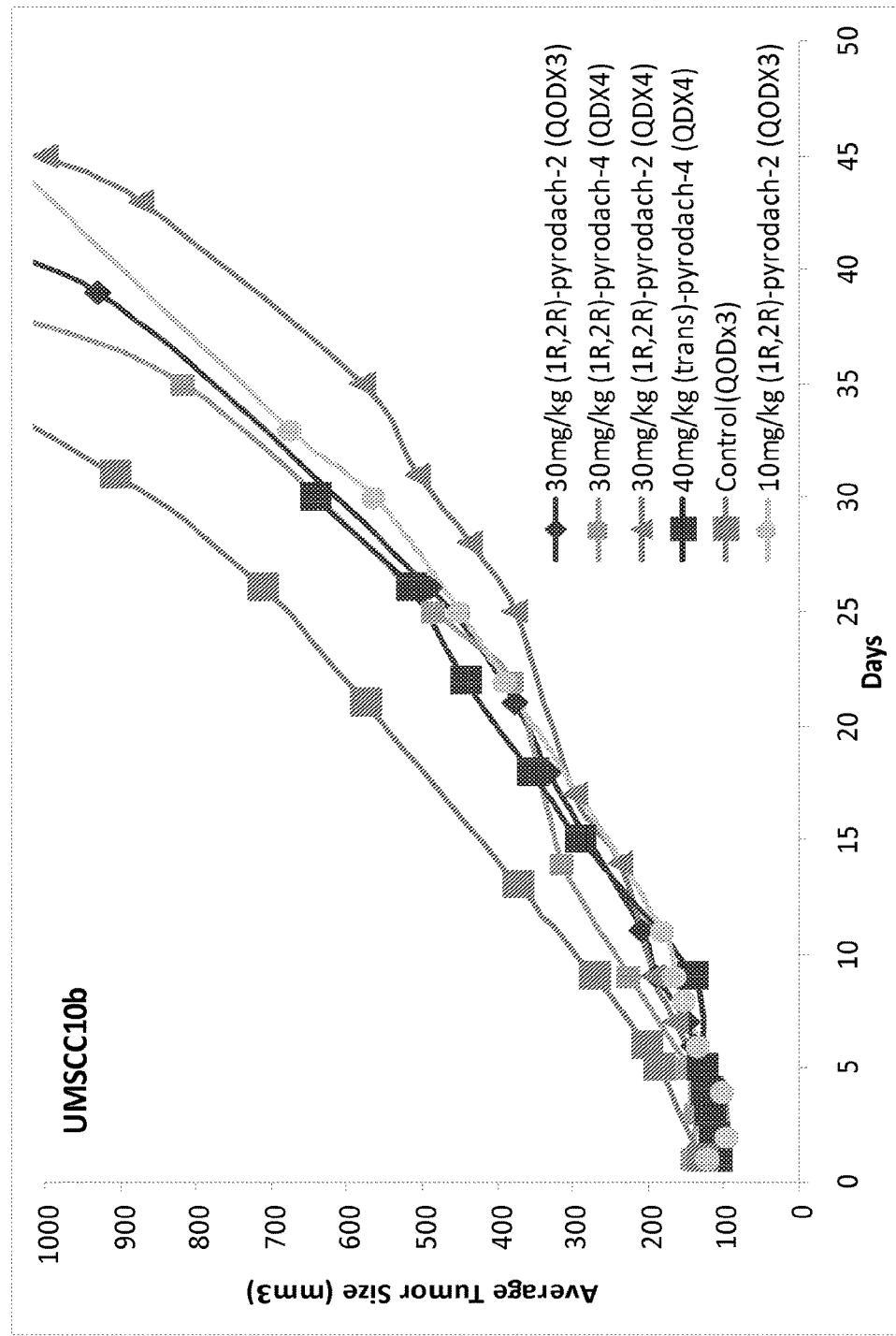
FIG. 7 shows efficacies of (1R,2R)-pyrodach-2 [administered qodx3 and once every day for four consecutive days ("qdx4")] and (1R,2R)-pyrodach-4 (administered qdx4), described in detail below, against human head-and-neck cancer (UMSCC10b).

Efficacy data of (1R,2R)-pyrodach-2 and (1R,2R)-pyrodach-4 against human head-and-neck cancer UMSCC10b are summarized in FIG. 7. Doses were administered qodx3 and/or qdx4, ranging from 10 mg/kg body weight to 40 mg/kg body weight. These efficacies were compared with the racemic form trans-(±)-pyrodach-4. The doses were administered when the tumor reached 100-200 mm$^3$ in size.

Example 15

Maximum Tolerated Doses of (1R,2R)-pyrodach-2 and (1R,2R)-pyrodach-4

To determine the maximum tolerated doses, toxicity experiments were conducted for (1R,2R)-pyrodach-2, (1R,2R)-pyrodach-4, trans-(±)-pyrodach-4, trans-(±)-pyrodach-4, cisplatin, and carboplatin. Escalating doses were administered from 10 mg/kg to 100 mg/kg in 4-5 week-old female ICR (CD-1) mice, Taconic(Rensselaer, N.Y.). The mice had body weights between 15 g and 24 g. The mice were injected with one of the phosphaplatins every other day in a three-dose regimen. Total body-weight loss of 20% or more, unthrifty appearance, failure to gain weight, other observable health issues, departures from normal behaviors, or death, were considered an adverse event.

At lower doses of 10 mg/kg, no loss of weight was observed. No death or loss of greater than 20% of body weight was observed up to the highest dose of 40 mg/kg for all phosphaplatin compounds. These results can be compared to cisplatin, for which 100% of the mice died at a dose of 12 mg/kg, and to carboplatin, for which 33% death was observed at a dose of 60 mg/kg. At higher doses of 100

Example 16

Quantitative Gene Expression from Real-Time PCR Experiments

Quantitative real-time PCR experiments were performed to estimate the expression of a few targeted genes. Human epithelial ovarian carcer cells (A2780) and cisplatin-resistant cells (A2780/C30) were cultured in RPMI 1640 with or without cisplatin, (1R,2R)-pyrodach-4, and trans-(±)-pyrodach-4 for 0, 3, 12 and 24 hours. Both treated and untreated cancer cells were maintained in RPMI 1640 medium with 10% fetal bovine serum, 2 µmol L-glutamine, 100 units/mL penicillin-streptomycin and 0.25 units/mL insulin solution, at 37° C. with 5% $CO_2$. RNA was isolated from cells, both the treated and untreated. Treated cells are those cells harvested after the exposure of cells to a phosphaplatin at its $IC_{50}$ value concentration at different time intervals, from three hours to 24 hrs.

The RNA samples were treated with DNase-free RNase (QIAGEN Sciences) to remove DNA. Then, cDNA was synthesized using the High Capacity RNA-to-cDNA kit (Applied Biosystems) according to the manufacturer's instructions. The quantity and purity of RNA were determined by UV spectroscopy (NanoDrop 2000 Thermo Scientific, Wilmington, Del.). A minimum absorbance ratio index (ratio of the absorbance measured at 260 nm over the absorbance measured at 280 nm) of 1.9 was used as an acceptable purity.

The isolated RNA samples were stored at −80° C. and were subjected to minimal freeze-thaw cycles to maintain RNA integrity. Duplex real-time PCRs were performed using Taqman® Gene Expression Assays for the target gene and endogenous control (β-actin) in the same reaction well. The endogenous control is the reference used to normalize the target mRNA. These chain reactions were initially performed using different cDNA concentrations to determine the optimal concentrations of cDNA required to detect the gene of interest. The target gene was labeled with a blue dye (FAM, absorbance: 494 nm, emission: 518 nm) while the reference gene was tagged with a green dye (VIC, absorbance: 538 nm, emission: 554 nm). The cDNA concentrations were selected such that the threshold cycle (Ct) values for the target genes were between 17 and 32, most sensitive for the fluorescence detection by ABI StepOnePlus™ instrument used for the measurements.

The threshold cycle number (Ct), the point at which the fluorescence of the qPCR reaction just exceeds the threshold fluorescence of the detection system, was determined. These Ct values were used to compare the levels of target genes and the endogenous controls. Quantitative gene expressions are reported in terms of fold-change ($2^{-\Delta\Delta Ct}$) which were calculated from $\Delta Ct$ and $\Delta\Delta Ct$ values according to the relationships: $\Delta Ct = (Ct_{target} - Ct_{reference})$ and $\Delta\Delta Ct = (\Delta Ct)_{time\ X} - (\Delta Ct)_{time\ zero\ (control)}$. The fold-expression for the control samples (untreated) remained equal to 1, because the value of $\Delta\Delta Ct = 0$, and, therefore, $2^0 = 1$.

This application should not be considered limited to the specific examples and embodiments described herein, but rather should be understood to cover all aspects of the invention. Various modifications, equivalent processes, as well as numerous structures and devices to which the present invention may be applicable will be readily apparent to those of skill in the art. Those skilled in the art will understand that various changes may be made without departing from the scope of the invention, which is not to be considered limited to what is described in the specification.

What is claimed is:

1. A phosphaplatin complex selected from the group consisting of:
   (iii) cis-pyrodach-2 having formula (III),

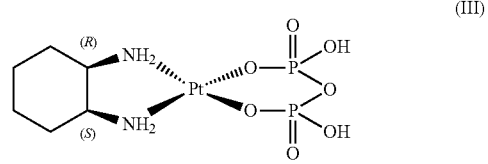

(III)

or pharmaceutically acceptable salt or solvate thereof; and
(vi) cis-pyrodach-4 having formula (VI),

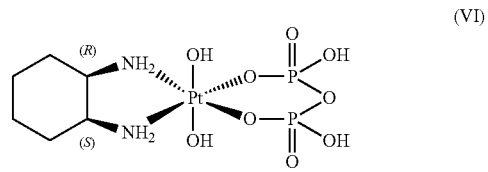

(VI)

or pharmaceutically acceptable salt or solvate thereof.

2. A composition for treating a proliferative disease, said composition comprising:
   (a) one or more phosphaplatin complexes selected from the group consisting of:
   (iii) cis-pyrodach-2 having formula (III):

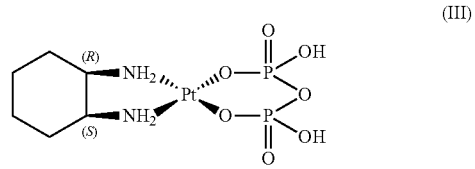

(III)

or pharmaceutically acceptable salts or solvates thereof;
   (vi) cis-pyrodach-4 having formula (VI):

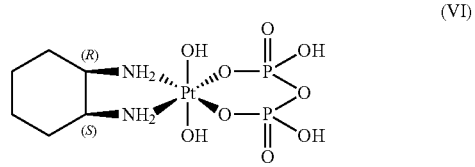

(VI)

or pharmaceutically acceptable salts or solvates thereof; and
   (vii) a multicomplex mixture of said phosphaplatin complexes of formula (III) and (VI) and
   (b) at least one pharmaceutically acceptable ingredient selected from the group consisting of carriers, diluents, adjuvants, and vehicles.

3. The composition of claim 2, wherein said phosphaplatin complexes are isolated, monomeric phosphaplatin complexes.

4. The composition of claim 2, further comprising enantioenriched pyrodach-2 having an enantiomeric excess of from 10% to 100% of (1R,2R)-pyrodach-2.

5. The composition of claim 4, wherein said enantioenriched pyrodach-2 consists of (1R,2R)-pyrodach-2 having formula (I) and (1S,2S)-pyrodach-2 having formula (II):

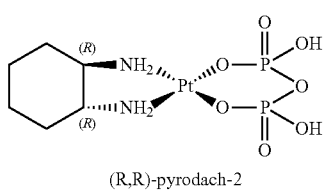

(R,R)-pyrodach-2

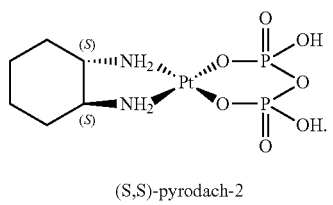

(S,S)-pyrodach-2

6. The composition of claim 2, further comprising enantioenriched pyrodach-2 having an enantiomeric excess of from 10% to 100% of (1S,2S)-pyrodach-2.

7. The composition of claim 6, wherein said enantioenriched pyrodach-2 consists of (1R,2R)-pyrodach-2 having formula (I) and (1S,2S)-pyrodach-2 having formula (II):

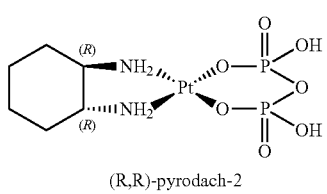

(R,R)-pyrodach-2

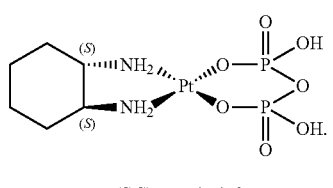

(S,S)-pyrodach-2

8. The composition of claim 2, further comprising enantioenriched pyrodach-4 having an enantiomeric excess of from 10% to 100% of (1R,2R)-pyrodach-4.

9. The composition of claim 8, wherein said enantioenriched pyrodach-4 consists of (1R,2R)-pyrodach-4 having formula (IV) and (1S,2S)-pyrodach-4 having formula (V):

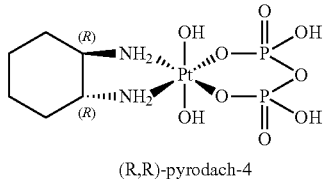

(R,R)-pyrodach-4

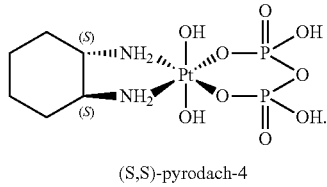

(S,S)-pyrodach-4

10. The composition of claim 2, further comprising enantioenriched pyrodach-4 having an enantiomeric excess of from 10% to 100% of (1S,2S)-pyrodach-4.

11. The composition of claim 10, wherein said enantioenriched pyrodach-4 consists of (1R,2R)-pyrodach-4 having formula (IV) and (1S,2S)-pyrodach-4 having formula (V):

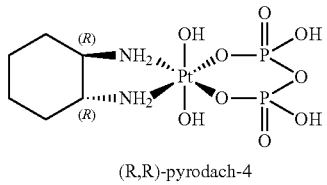

(R,R)-pyrodach-4

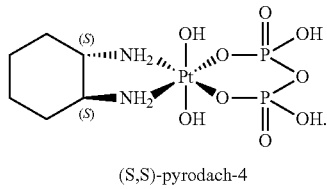

(S,S)-pyrodach-4

12. The composition of claim 2, comprising cis-pyrodach-2.

13. The composition of claim 2, comprising cis-pyrodach-4.

14. The composition of claim 2, wherein said proliferative disease is a cancer.

15. The composition of claim 2, wherein said proliferative disease is selected from ovarian cancer, testicular cancer, small-cell lung cancer, non-small-cell lung cancer, head-and-neck cancers, skin cancer, pancreatic cancer, breast cancer, glioblastoma cancer, and colon cancer.

16. The composition of claim 2, wherein said proliferative disease is a cancer resistant to treatment by at least one of cisplatin, carboplatin, and oxaliplatin.

* * * * *